US010308963B2

(12) United States Patent
Headman et al.

(10) Patent No.: US 10,308,963 B2
(45) Date of Patent: Jun. 4, 2019

(54) PROCESSES OF PRODUCING ETHANOL USING A FERMENTING ORGANISM

(71) Applicants: Novozymes A/S, Bagsvaerd (DK); Microbiogen Pty. Ltd., Sydney (AU)

(72) Inventors: Jennifer Headman, Raleigh, NC (US); Jeremy Saunders, Raleigh, NC (US); Ryan Schron, Rolesville, NC (US); Paul Victor Attfield, Mount Colah (AU); Philip John Livingstone Bell, Turramurra (AU)

(73) Assignees: Novozymes A/S, Bagsvaerd (DK); Microbiogen Pty. Ltd., Sydney (AU)

( * ) Notice: Subject to any disclaimer, the term of this patent is extended or adjusted under 35 U.S.C. 154(b) by 0 days.

(21) Appl. No.: 15/553,206

(22) PCT Filed: Feb. 26, 2016

(86) PCT No.: PCT/US2016/019874
§ 371 (c)(1),
(2) Date: Aug. 24, 2017

(87) PCT Pub. No.: WO2016/138437
PCT Pub. Date: Sep. 1, 2016

(65) Prior Publication Data
US 2018/0073040 A1    Mar. 15, 2018

Related U.S. Application Data

(60) Provisional application No. 62/121,925, filed on Feb. 27, 2015.

(51) Int. Cl.
*C12P 7/06* (2006.01)
*C12N 1/18* (2006.01)
*C12N 15/01* (2006.01)
*C12R 1/865* (2006.01)

(52) U.S. Cl.
CPC .................. *C12P 7/06* (2013.01); *C12N 1/18* (2013.01); *C12N 15/01* (2013.01); *C12R 1/865* (2013.01); *Y02E 50/17* (2013.01)

(58) Field of Classification Search
None
See application file for complete search history.

(56) References Cited

FOREIGN PATENT DOCUMENTS

| WO | 2005121337 A1 | 12/2005 |
| WO | 2010008841 A2 | 1/2010 |
| WO | WO2010008841 | * 1/2010 |
| WO | 2011035392 A1 | 3/2011 |

OTHER PUBLICATIONS

Zhang et al, 2012, Biotechnol for Biofuels, 5(1), 46.

* cited by examiner

*Primary Examiner* — Christian L Fronda
(74) *Attorney, Agent, or Firm* — Eric J. Fechter

(57) ABSTRACT

The invention relates to improved processes of producing ethanol from starch-containing material wherein saccharification and/or fermentation is done at a temperature below the initial gelatinization temperature in the presence of glucoamylase and alpha-amylase, and optionally a protease and/or a cellulolytic enzyme composition; wherein the fermenting organism is a *Saccharomyces* yeast strain providing a higher ethanol yield boost and lower glycerol production compared to ETHANOL RED™ under the same fermentation conditions. The invention also relates to *Saccharomyces* yeast strains and derivatives thereof, as well as compositions comprising such yeast strains, suitable for use in a process of the invention.

16 Claims, No Drawings
Specification includes a Sequence Listing.

SEQUENCE LISTING

```
<160> NUMBER OF SEQ ID NOS: 18

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125
```

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
            275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 2
<211> LENGTH: 1068

```
<212> TYPE: DNA
<213> ORGANISM: Thermoascus aurantiacus
<220> FEATURE:
<221> NAME/KEY: CDS
<222> LOCATION: (1)..(1065)
<220> FEATURE:
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2
```

| atg | cgg | ctc | gtt | gct | tcc | cta | acg | gcc | ttg | gtg | gcc | ttg | tcc | gta | 45 |
|---|---|---|---|---|---|---|---|---|---|---|---|---|---|---|---|
| Met | Arg | Leu | Val | Ala | Ser | Leu | Thr | Ala | Leu | Val | Ala | Leu | Ser | Val | |
| | -175 | | | | | -170 | | | | | -165 | | | | |

| cct | gtc | ttt | ccc | gct | gct | gtc | aac | gtg | aag | cgt | gct | tcg | tcc | tac | 90 |
|---|---|---|---|---|---|---|---|---|---|---|---|---|---|---|---|
| Pro | Val | Phe | Pro | Ala | Ala | Val | Asn | Val | Lys | Arg | Ala | Ser | Ser | Tyr | |
| | | -160 | | | | | -155 | | | | | -150 | | | |

| ctg | gag | atc | act | ctg | agc | cag | gtc | agc | aac | act | ctg | atc | aag | gcc | 135 |
|---|---|---|---|---|---|---|---|---|---|---|---|---|---|---|---|
| Leu | Glu | Ile | Thr | Leu | Ser | Gln | Val | Ser | Asn | Thr | Leu | Ile | Lys | Ala | |
| | | | -145 | | | | | -140 | | | | | -135 | | |

| gtg | gtc | cag | aac | act | ggt | agc | gac | gag | ttg | tcc | ttc | gtt | cac | ctg | 180 |
|---|---|---|---|---|---|---|---|---|---|---|---|---|---|---|---|
| Val | Val | Gln | Asn | Thr | Gly | Ser | Asp | Glu | Leu | Ser | Phe | Val | His | Leu | |
| | | | -130 | | | | | -125 | | | | | -120 | | |

| aac | ttc | ttc | aag | gac | ccc | gct | cct | gtc | aaa | aag | gta | tcg | gtc | tat | 225 |
|---|---|---|---|---|---|---|---|---|---|---|---|---|---|---|---|
| Asn | Phe | Phe | Lys | Asp | Pro | Ala | Pro | Val | Lys | Lys | Val | Ser | Val | Tyr | |
| | | | -115 | | | | | -110 | | | | | -105 | | |

| cgc | gat | ggg | tct | gaa | gtg | cag | ttc | gag | ggc | att | ttg | agc | cgc | tac | aaa | 273 |
|---|---|---|---|---|---|---|---|---|---|---|---|---|---|---|---|---|
| Arg | Asp | Gly | Ser | Glu | Val | Gln | Phe | Glu | Gly | Ile | Leu | Ser | Arg | Tyr | Lys | |
| | | | -100 | | | | | -95 | | | | | -90 | | | |

| tcg | act | ggc | ctc | tct | cgt | gac | gcc | ttt | act | tat | ctg | gct | ccc | gga | gag | 321 |
|---|---|---|---|---|---|---|---|---|---|---|---|---|---|---|---|---|
| Ser | Thr | Gly | Leu | Ser | Arg | Asp | Ala | Phe | Thr | Tyr | Leu | Ala | Pro | Gly | Glu | |
| | | -85 | | | | | -80 | | | | | -75 | | | | |

| tcc | gtc | gag | gac | gtt | ttt | gat | att | gct | tcg | act | tac | gat | ctg | acc | agc | 369 |
|---|---|---|---|---|---|---|---|---|---|---|---|---|---|---|---|---|
| Ser | Val | Glu | Asp | Val | Phe | Asp | Ile | Ala | Ser | Thr | Tyr | Asp | Leu | Thr | Ser | |
| | | -70 | | | | | -65 | | | | | -60 | | | | |

| ggc | ggc | cct | gta | act | atc | cgt | act | gag | gga | gtt | gtt | ccc | tac | gcc | acg | 417 |
|---|---|---|---|---|---|---|---|---|---|---|---|---|---|---|---|---|
| Gly | Gly | Pro | Val | Thr | Ile | Arg | Thr | Glu | Gly | Val | Val | Pro | Tyr | Ala | Thr | |
| -55 | | | | | -50 | | | | | -45 | | | | | -40 | |

| gct | aac | agc | act | gat | att | gcc | ggc | tac | atc | tca | tac | tcg | tct | aat | gtg | 465 |
|---|---|---|---|---|---|---|---|---|---|---|---|---|---|---|---|---|
| Ala | Asn | Ser | Thr | Asp | Ile | Ala | Gly | Tyr | Ile | Ser | Tyr | Ser | Ser | Asn | Val | |
| | | | -35 | | | | | -30 | | | | | -25 | | | |

| ttg | acc | att | gat | gtc | gat | ggc | gcc | gct | gct | gcc | act | gtc | tcc | aag | gca | 513 |
|---|---|---|---|---|---|---|---|---|---|---|---|---|---|---|---|---|
| Leu | Thr | Ile | Asp | Val | Asp | Gly | Ala | Ala | Ala | Ala | Thr | Val | Ser | Lys | Ala | |
| | | | -20 | | | | | -15 | | | | | -10 | | | |

| atc | act | cct | ttg | gac | cgc | cgc | act | agg | atc | agt | tcc | tgc | tcc | ggc | agc | 561 |
|---|---|---|---|---|---|---|---|---|---|---|---|---|---|---|---|---|
| Ile | Thr | Pro | Leu | Asp | Arg | Arg | Thr | Arg | Ile | Ser | Ser | Cys | Ser | Gly | Ser | |
| | | -5 | | | | | -1 | 1 | | | | 5 | | | | |

| aga | cag | agc | gct | ctt | act | acg | gct | ctc | aga | aac | gct | gct | tct | ctt | gcc | 609 |
|---|---|---|---|---|---|---|---|---|---|---|---|---|---|---|---|---|
| Arg | Gln | Ser | Ala | Leu | Thr | Thr | Ala | Leu | Arg | Asn | Ala | Ala | Ser | Leu | Ala | |
| 10 | | | | | 15 | | | | | 20 | | | | | 25 | |

| aac | gca | gct | gcc | gac | gcg | gct | cag | tct | gga | tca | gct | tca | aag | ttc | agc | 657 |
|---|---|---|---|---|---|---|---|---|---|---|---|---|---|---|---|---|
| Asn | Ala | Ala | Ala | Asp | Ala | Ala | Gln | Ser | Gly | Ser | Ala | Ser | Lys | Phe | Ser | |
| | | | 30 | | | | | 35 | | | | | 40 | | | |

| gag | tac | ttc | aag | act | act | tct | agc | tct | acc | cgc | cag | acc | gtg | gct | gcg | 705 |
|---|---|---|---|---|---|---|---|---|---|---|---|---|---|---|---|---|
| Glu | Tyr | Phe | Lys | Thr | Thr | Ser | Ser | Ser | Thr | Arg | Gln | Thr | Val | Ala | Ala | |
| | | | 45 | | | | | 50 | | | | | 55 | | | |

| cgt | ctt | cgg | gct | gtt | gcg | cgg | gag | gca | tct | tcg | tct | tct | tcg | gga | gcc | 753 |
|---|---|---|---|---|---|---|---|---|---|---|---|---|---|---|---|---|
| Arg | Leu | Arg | Ala | Val | Ala | Arg | Glu | Ala | Ser | Ser | Ser | Ser | Ser | Gly | Ala | |

```
              60                    65                    70
acc acg tac tac tgc gac gat ccc tac ggc tac tgt tcc tcc aac gtc      801
Thr Thr Tyr Tyr Cys Asp Asp Pro Tyr Gly Tyr Cys Ser Ser Asn Val
     75                   80                   85 ctg gct tac acc ctg cct tca tac aac ata atc gcc aac tgt gac att      849
Leu Ala Tyr Thr Leu Pro Ser Tyr Asn Ile Ile Ala Asn Cys Asp Ile
 90                   95                  100                  105 ttc tat act tac ctg ccg gct ctg acc agt acc tgt cac gct cag gat      897
Phe Tyr Thr Tyr Leu Pro Ala Leu Thr Ser Thr Cys His Ala Gln Asp
                    110                  115                  120 caa gcg acc act gcc ctt cac gag ttc acc cat gcg cct ggc gtc tac      945
Gln Ala Thr Thr Ala Leu His Glu Phe Thr His Ala Pro Gly Val Tyr
            125                  130                  135 agc cct ggc acg gac gac ctg gcg tat ggc tac cag gct gcg atg ggt      993
Ser Pro Gly Thr Asp Asp Leu Ala Tyr Gly Tyr Gln Ala Ala Met Gly
        140                  145                  150 ctc agc agc agc cag gct gtc atg aac gct gac acc tac gct ctc tat     1041
Leu Ser Ser Ser Gln Ala Val Met Asn Ala Asp Thr Tyr Ala Leu Tyr
    155                  160                  165 gcg aat gcc ata tac ctt ggt tgc taa                                  1068
Ala Asn Ala Ile Tyr Leu Gly Cys
170                 175

<210> SEQ ID NO 3
<211> LENGTH: 355
<212> TYPE: PRT
<213> ORGANISM: Thermoascus aurantiacus

<400> SEQUENCE: 3

Met Arg Leu Val  Ala Ser Leu Thr  Ala Leu Val Ala  Leu Ser Val
            -175                 -170                 -165

Pro Val Phe Pro  Ala Ala Val Asn  Val Lys Arg Ala  Ser Ser Tyr
            -160                 -155                 -150

Leu Glu Ile Thr  Leu Ser Gln Val  Ser Asn Thr Leu  Ile Lys Ala
            -145                 -140                 -135

Val Val Gln Asn  Thr Gly Ser Asp  Glu Leu Ser Phe  Val His Leu
            -130                 -125                 -120

Asn Phe Phe Lys  Asp Pro Ala Pro  Val Lys Lys Val  Ser Val Tyr
            -115                 -110                 -105

Arg Asp Gly Ser  Glu Val Gln Phe  Glu Gly Ile Leu  Ser Arg Tyr Lys
            -100                  -95                  -90

Ser Thr Gly Leu  Ser Arg Asp Ala  Phe Thr Tyr Leu  Ala Pro Gly Glu
             -85                  -80                  -75

Ser Val Glu Asp  Val Phe Asp Ile  Ala Ser Thr Tyr  Asp Leu Thr Ser
             -70                  -65                  -60

Gly Gly Pro Val  Thr Ile Arg Thr  Glu Gly Val Val  Pro Tyr Ala Thr
-55                               -50                  -45                  -40

Ala Asn Ser Thr  Asp Ile Ala Gly  Tyr Ile Ser Tyr  Ser Ser Asn Val
                  -35                  -30                  -25

Leu Thr Ile Asp  Val Asp Gly Ala  Ala Ala Thr Val  Ser Lys Ala
                  -20                  -15                  -10

Ile Thr Pro Leu  Asp Arg Arg Thr  Arg Ile Ser Ser  Cys Ser Gly Ser
              -5                   -1  1                    5

Arg Gln Ser Ala  Leu Thr Thr Ala  Leu Arg Asn Ala  Ala Ser Leu Ala
10                                 15                   20                   25

Asn Ala Ala Ala  Asp Ala Ala Gln  Ser Gly Ser Ala  Ser Lys Phe Ser
                   30                   35                   40
```

```
Glu Tyr Phe Lys Thr Thr Ser Ser Thr Arg Gln Thr Val Ala Ala
            45                  50                  55

Arg Leu Arg Ala Val Ala Arg Glu Ala Ser Ser Ser Ser Gly Ala
            60                  65                  70

Thr Thr Tyr Tyr Cys Asp Asp Pro Tyr Gly Tyr Cys Ser Ser Asn Val
 75                  80                  85

Leu Ala Tyr Thr Leu Pro Ser Tyr Asn Ile Ile Ala Asn Cys Asp Ile
 90                  95                 100                 105

Phe Tyr Thr Tyr Leu Pro Ala Leu Thr Ser Thr Cys His Ala Gln Asp
                110                 115                 120

Gln Ala Thr Thr Ala Leu His Glu Phe Thr His Ala Pro Gly Val Tyr
            125                 130                 135

Ser Pro Gly Thr Asp Asp Leu Ala Tyr Gly Tyr Gln Ala Ala Met Gly
            140                 145                 150

Leu Ser Ser Ser Gln Ala Val Met Asn Ala Asp Thr Tyr Ala Leu Tyr
            155                 160                 165

Ala Asn Ala Ile Tyr Leu Gly Cys
170                 175

<210> SEQ ID NO 4
<211> LENGTH: 573
<212> TYPE: PRT
<213> ORGANISM: Gloeophyllum sepiarium

<400> SEQUENCE: 4

Met Tyr Arg Phe Leu Val Cys Ala Leu Gly Leu Ala Ala Ser Val Leu
 1               5                  10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
            35                  40                  45

Ala Ser Ala Gly Val Val Val Ala Ser Pro Ser Thr Ser Asp Pro Asp
 50                  55                  60

Tyr Trp Tyr Thr Trp Thr Arg Asp Ser Ser Leu Val Phe Lys Ser Leu
 65                  70                  75                  80

Ile Asp Gln Tyr Thr Thr Gly Ile Asp Ser Thr Ser Ser Leu Arg Thr
            85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
            115                 120                 125

Asn Val Asp Glu Thr Ala Phe Thr Gly Ala Trp Gly Arg Pro Gln Arg
            130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
            165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Phe Phe Thr Thr
            195                 200                 205

Ala Val Gln His Arg Ala Leu Arg Glu Gly Ala Ala Phe Ala Thr Ala
            210                 215                 220

Ile Gly Gln Thr Ser Gln Val Ser Ser Tyr Thr Thr Gln Ala Asp Asn
```

225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Glu Asn Asp Thr Trp Arg
                565                 570

<210> SEQ ID NO 5
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 5

Ala Glu Leu Glu Gly Leu Asp Glu Ser Ala Ala Gln Val Met Ala Thr
1               5                   10                  15

```
Tyr Val Trp Asn Leu Gly Tyr Asp Gly Ser Gly Ile Thr Ile Gly Ile
             20                  25                  30
Ile Asp Thr Gly Ile Asp Ala Ser His Pro Asp Leu Gln Gly Lys Val
         35                  40                  45
Ile Gly Trp Val Asp Phe Val Asn Gly Arg Ser Tyr Pro Tyr Asp Asp
 50                  55                  60
His Gly His Gly Thr His Val Ala Ser Ile Ala Ala Gly Thr Gly Ala
 65                  70                  75                  80
Ala Ser Asn Gly Lys Tyr Lys Gly Met Ala Pro Gly Ala Lys Leu Ala
                 85                  90                  95
Gly Ile Lys Val Leu Gly Ala Asp Gly Ser Gly Ser Ile Ser Thr Ile
            100                 105                 110
Ile Lys Gly Val Glu Trp Ala Val Asp Asn Lys Asp Lys Tyr Gly Ile
        115                 120                 125
Lys Val Ile Asn Leu Ser Leu Gly Ser Ser Gln Ser Ser Asp Gly Thr
130                 135                 140
Asp Ala Leu Ser Gln Ala Val Asn Ala Ala Trp Asp Ala Gly Leu Val
145                 150                 155                 160
Val Val Val Ala Ala Gly Asn Ser Gly Pro Asn Lys Tyr Thr Ile Gly
                165                 170                 175
Ser Pro Ala Ala Ala Ser Lys Val Ile Thr Val Gly Ala Val Asp Lys
            180                 185                 190
Tyr Asp Val Ile Thr Ser Phe Ser Arg Gly Pro Thr Ala Asp Gly
        195                 200                 205
Arg Leu Lys Pro Glu Val Val Ala Pro Gly Asn Trp Ile Ile Ala Ala
210                 215                 220
Arg Ala Ser Gly Thr Ser Met Gly Gln Pro Ile Asn Asp Tyr Tyr Thr
225                 230                 235                 240
Ala Ala Pro Gly Thr Ser Met Ala Thr Pro His Val Ala Gly Ile Ala
                245                 250                 255
Ala Leu Leu Leu Gln Ala His Pro Ser Trp Thr Pro Asp Lys Val Lys
            260                 265                 270
Thr Ala Leu Ile Glu Thr Ala Asp Ile Val Lys Pro Asp Glu Ile Ala
        275                 280                 285
Asp Ile Ala Tyr Gly Ala Gly Arg Val Asn Ala Tyr Lys Ala Ile Asn
290                 295                 300
Tyr Asp Asn Tyr Ala Lys Leu Val Phe Thr Gly Tyr Val Ala Asn Lys
305                 310                 315                 320
Gly Ser Gln Thr His Gln Phe Val Ile Ser Gly Ala Ser Phe Val Thr
                325                 330                 335
Ala Thr Leu Tyr Trp Asp Asn Ala Asn Ser Asp Leu Asp Leu Tyr Leu
            340                 345                 350
Tyr Asp Pro Asn Gly Asn Gln Val Asp Tyr Ser Tyr Thr Ala Tyr Tyr
        355                 360                 365
Gly Phe Glu Lys Val Gly Tyr Tyr Asn Pro Thr Asp Gly Thr Trp Thr
370                 375                 380
Ile Lys Val Val Ser Tyr Ser Gly Ser Ala Asn Tyr Gln Val Asp Val
385                 390                 395                 400
Val Ser Asp Gly Ser Leu Ser Gln Pro Gly Ser Ser
                405                 410

<210> SEQ ID NO 6
<211> LENGTH: 532
```

<212> TYPE: PRT
<213> ORGANISM: Aspergillus fumigatus

<400> SEQUENCE: 6

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Val Gly Thr Ser
            20                  25                  30

Gln Ala Glu Val His Pro Ser Met Thr Trp Gln Ser Cys Thr Ala Gly
            35                  40                  45

Gly Ser Cys Thr Thr Asn Asn Gly Lys Val Val Ile Asp Ala Asn Trp
        50                  55                  60

Arg Trp Val His Lys Val Gly Asp Tyr Thr Asn Cys Tyr Thr Gly Asn
65              70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
290                 295                 300

Thr Val Asp Thr Lys Ser Lys Phe Thr Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
370                 375                 380

Met Gly Ala Ala Leu Ala Gln Gly Met Val Leu Val Met Ser Leu Trp
385                 390                 395                 400
```

```
Asp Asp His Ser Ala Asn Met Leu Trp Leu Asp Ser Asn Tyr Pro Thr
            405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
            435                 440                 445

Val Val Tyr Ser Asn Ile Lys Val Gly Pro Ile Gly Ser Thr Phe Asn
            450                 455                 460

Ser Gly Gly Ser Asn Pro Gly Gly Thr Thr Thr Thr Thr Thr Thr Thr
465                 470                 475                 480

Gln Pro Thr Thr Thr Thr Thr Ala Gly Asn Pro Gly Gly Thr Gly
            485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
            515                 520                 525

Ser Gln Cys Leu
    530

<210> SEQ ID NO 7
<211> LENGTH: 454
<212> TYPE: PRT
<213> ORGANISM: Aspergillus fumigatus

<400> SEQUENCE: 7

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
            35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
            85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
            115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
            165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
            195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
```

```
            225                 230                 235                 240

Val Ala Lys Cys Ala Asn Ala Gln Ser Ala Tyr Leu Glu Cys Val Asp
                    245                 250                 255

Tyr Ala Leu Lys Gln Leu Asn Leu Pro Asn Val Ala Met Tyr Leu Asp
                    260                 265                 270

Ala Gly His Ala Gly Trp Leu Gly Trp Pro Ala Asn Leu Gly Pro Ala
                    275                 280                 285

Ala Thr Leu Phe Ala Lys Val Tyr Thr Asp Ala Gly Ser Pro Ala Ala
            290                 295                 300

Val Arg Gly Leu Ala Thr Asn Val Ala Asn Tyr Asn Ala Trp Ser Leu
    305                 310                 315                 320

Ser Thr Cys Pro Ser Tyr Thr Gln Gly Asp Pro Asn Cys Asp Glu Lys
                    325                 330                 335

Lys Tyr Ile Asn Ala Met Ala Pro Leu Leu Lys Glu Ala Gly Phe Asp
                    340                 345                 350

Ala His Phe Ile Met Asp Thr Ser Arg Asn Gly Val Gln Pro Thr Lys
                    355                 360                 365

Gln Asn Ala Trp Gly Asp Trp Cys Asn Val Ile Gly Thr Gly Phe Gly
            370                 375                 380

Val Arg Pro Ser Thr Asn Thr Gly Asp Pro Leu Gln Asp Ala Phe Val
    385                 390                 395                 400

Trp Ile Lys Pro Gly Gly Glu Ser Asp Gly Thr Ser Asn Ser Thr Ser
                    405                 410                 415

Pro Arg Tyr Asp Ala His Cys Gly Tyr Ser Asp Ala Leu Gln Pro Ala
                    420                 425                 430

Pro Glu Ala Gly Thr Trp Phe Gln Ala Tyr Phe Glu Gln Leu Leu Thr
            435                 440                 445

Asn Ala Asn Pro Ser Phe
            450

<210> SEQ ID NO 8
<211> LENGTH: 863
<212> TYPE: PRT
<213> ORGANISM: Aspergillus fumigatus

<400> SEQUENCE: 8

Met Arg Phe Gly Trp Leu Glu Val Ala Ala Leu Thr Ala Ala Ser Val
    1               5                   10                  15

Ala Asn Ala Gln Glu Leu Ala Phe Ser Pro Pro Phe Tyr Pro Ser Pro
                    20                  25                  30

Trp Ala Asp Gly Gln Gly Glu Trp Ala Asp Ala His Arg Arg Ala Val
                    35                  40                  45

Glu Ile Val Ser Gln Met Thr Leu Ala Glu Lys Val Asn Leu Thr Thr
            50                  55                  60

Gly Thr Gly Trp Glu Met Asp Arg Cys Val Gly Gln Thr Gly Ser Val
    65                  70                  75                  80

Pro Arg Leu Gly Ile Asn Trp Gly Leu Cys Gly Gln Asp Ser Pro Leu
                    85                  90                  95

Gly Ile Arg Phe Ser Asp Leu Asn Ser Ala Phe Pro Ala Gly Thr Asn
                    100                 105                 110

Val Ala Ala Thr Trp Asp Lys Thr Leu Ala Tyr Leu Arg Gly Lys Ala
                    115                 120                 125

Met Gly Glu Glu Phe Asn Asp Lys Gly Val Asp Ile Leu Leu Gly Pro
            130                 135                 140
```

-continued

```
Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
            165                 170                 175

Ile Lys Gly Ile Gln Asp Ala Gly Val Ile Ala Thr Ala Lys His Tyr
        180                 185                 190

Ile Leu Asn Glu Gln Glu His Phe Arg Gln Val Gly Glu Ala Gln Gly
    195                 200                 205

Tyr Gly Tyr Asn Ile Thr Glu Thr Ile Ser Ser Asn Val Asp Asp Lys
210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
            245                 250                 255

Gly Cys Gln Asn Ser Gln Thr Leu Asn Lys Leu Leu Lys Ala Glu Leu
        260                 265                 270

Gly Phe Gln Gly Phe Val Met Ser Asp Trp Ser Ala His His Ser Gly
    275                 280                 285

Val Gly Ala Ala Leu Ala Gly Leu Asp Met Ser Met Pro Gly Asp Ile
290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
            325                 330                 335

Arg Ile Met Thr Ala Tyr Tyr Lys Val Gly Arg Asp Arg Leu Arg Ile
        340                 345                 350

Pro Pro Asn Phe Ser Ser Trp Thr Arg Asp Glu Tyr Gly Trp Glu His
    355                 360                 365

Ser Ala Val Ser Glu Gly Ala Trp Thr Lys Val Asn Asp Phe Val Asn
370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
            405                 410                 415

Val Lys Val Gly Val Leu Gly Glu Asp Ala Gly Ser Asn Pro Trp Gly
        420                 425                 430

Ala Asn Gly Cys Pro Asp Arg Gly Cys Asp Asn Gly Thr Leu Ala Met
    435                 440                 445

Ala Trp Gly Ser Gly Thr Ala Asn Phe Pro Tyr Leu Val Thr Pro Glu
450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
        500                 505                 510

Ile Ser Val Asp Gly Asn Glu Gly Asp Arg Lys Asn Leu Thr Leu Trp
    515                 520                 525

Lys Asn Gly Glu Ala Val Ile Asp Thr Val Val Ser His Cys Asn Asn
530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
```

```
                        565                 570                 575
Gln Glu Ser Gly Asn Ser Leu Val Asp Val Leu Tyr Gly Arg Val Asn
                    580                 585                 590
Pro Ser Ala Lys Thr Pro Phe Thr Trp Gly Lys Thr Arg Glu Ser Tyr
                595                 600                 605
Gly Ala Pro Leu Leu Thr Glu Pro Asn Asn Gly Asn Gly Ala Pro Gln
            610                 615                 620
Asp Asp Phe Asn Glu Gly Val Phe Ile Asp Tyr Arg His Phe Asp Lys
625                 630                 635                 640
Arg Asn Glu Thr Pro Ile Tyr Glu Phe Gly His Gly Leu Ser Tyr Thr
                645                 650                 655
Thr Phe Gly Tyr Ser His Leu Arg Val Gln Ala Leu Asn Ser Ser Ser
                660                 665                 670
Ser Ala Tyr Val Pro Thr Ser Gly Glu Thr Lys Pro Ala Pro Thr Tyr
            675                 680                 685
Gly Glu Ile Gly Ser Ala Ala Asp Tyr Leu Tyr Pro Glu Gly Leu Lys
            690                 695                 700
Arg Ile Thr Lys Phe Ile Tyr Pro Trp Leu Asn Ser Thr Asp Leu Glu
705                 710                 715                 720
Asp Ser Ser Asp Asp Pro Asn Tyr Gly Trp Glu Asp Ser Glu Tyr Ile
                725                 730                 735
Pro Glu Gly Ala Arg Asp Gly Ser Pro Gln Pro Leu Leu Lys Ala Gly
            740                 745                 750
Gly Ala Pro Gly Gly Asn Pro Thr Leu Tyr Gln Asp Leu Val Arg Val
            755                 760                 765
Ser Ala Thr Ile Thr Asn Thr Gly Asn Val Ala Gly Tyr Glu Val Pro
770                 775                 780
Gln Leu Tyr Val Ser Leu Gly Gly Pro Asn Glu Pro Arg Val Val Leu
785                 790                 795                 800
Arg Lys Phe Asp Arg Ile Phe Leu Ala Pro Gly Glu Gln Lys Val Trp
                805                 810                 815
Thr Thr Thr Leu Asn Arg Arg Asp Leu Ala Asn Trp Asp Val Glu Ala
                820                 825                 830
Gln Asp Trp Val Ile Thr Lys Tyr Pro Lys Lys Val His Val Gly Ser
            835                 840                 845
Ser Ser Arg Lys Leu Pro Leu Arg Ala Pro Leu Pro Arg Val Tyr
            850                 855                 860

<210> SEQ ID NO 9
<211> LENGTH: 250
<212> TYPE: PRT
<213> ORGANISM: Thermoascus aurantiacus
<220> FEATURE:
<221> NAME/KEY: SIGNAL
<222> LOCATION: (1)..(22)

<400> SEQUENCE: 9

Met Ser Phe Ser Lys Ile Ile Ala Thr Ala Gly Val Leu Ala Ser Ala
1               5                   10                  15
Ser Leu Val Ala Gly His Gly Phe Val Gln Asn Ile Val Ile Asp Gly
            20                  25                  30
Lys Lys Tyr Tyr Gly Gly Tyr Leu Val Asn Gln Tyr Pro Tyr Met Ser
            35                  40                  45
Asn Pro Pro Glu Val Ile Ala Trp Ser Thr Thr Ala Thr Asp Leu Gly
        50                  55                  60
```

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250

<210> SEQ ID NO 10
<211> LENGTH: 253
<212> TYPE: PRT
<213> ORGANISM: Penicillium emersonii
<220> FEATURE:
<221> NAME/KEY: SIGNAL
<222> LOCATION: (1)..(25)

<400> SEQUENCE: 10

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
                20                  25                  30

Val Ile Gly Asp Gln Phe Tyr Ser Gly Tyr Ile Val Asn Ser Phe Pro
            35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

```
Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Ser Asp Ala Pro Glu Gly Thr Leu Gly Glu Asp Leu
210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 11
<211> LENGTH: 618
<212> TYPE: PRT
<213> ORGANISM: Talaromyces emersonii

<400> SEQUENCE: 11

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
            20                  25                  30

Asp Ser Phe Leu Ala Thr Glu Thr Pro Ile Ala Leu Gln Gly Val Leu
        35                  40                  45

Asn Asn Ile Gly Pro Asn Gly Ala Asp Val Ala Gly Ala Ser Ala Gly
    50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
    130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
        195                 200                 205

Val Glu Gly Ser Ser Phe Phe Thr Thr Ala Val Gln His Arg Ala Leu
    210                 215                 220

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
        275                 280                 285

Gly Gly Cys Asp Asp Ser Thr Phe Gln Pro Cys Ser Ala Arg Ala Leu
```

```
            290                 295                 300
Ala Asn His Lys Val Val Thr Asp Ser Phe Arg Ser Ile Tyr Ala Ile
305                 310                 315                 320

Asn Ser Gly Ile Ala Glu Gly Ser Ala Val Ala Val Gly Arg Tyr Pro
                325                 330                 335

Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Lys Lys Ile Gly
        355                 360                 365

Ser Ile Ser Ile Thr Asp Val Ser Leu Pro Phe Phe Gln Asp Ile Tyr
    370                 375                 380

Pro Ser Ala Ala Val Gly Thr Tyr Asn Ser Gly Ser Thr Thr Phe Asn
385                 390                 395                 400

Asp Ile Ile Ser Ala Val Gln Thr Tyr Gly Asp Gly Tyr Leu Ser Ile
                405                 410                 415

Val Glu Lys Tyr Thr Pro Ser Asp Gly Ser Leu Thr Glu Gln Phe Ser
            420                 425                 430

Arg Thr Asp Gly Thr Pro Leu Ser Ala Ser Ala Leu Thr Trp Ser Tyr
        435                 440                 445

Ala Ser Leu Leu Thr Ala Ser Ala Arg Arg Gln Ser Val Val Pro Ala
    450                 455                 460

Ser Trp Gly Glu Ser Ser Ala Ser Ser Val Pro Ala Val Cys Ser Ala
465                 470                 475                 480

Thr Ser Ala Thr Gly Pro Tyr Ser Thr Ala Thr Asn Thr Val Trp Pro
                485                 490                 495

Ser Ser Gly Ser Gly Ser Ser Thr Thr Thr Ser Ser Ala Pro Cys Thr
            500                 505                 510

Thr Pro Thr Ser Val Ala Val Thr Phe Asp Glu Ile Val Ser Thr Ser
        515                 520                 525

Tyr Gly Glu Thr Ile Tyr Leu Ala Gly Ser Ile Pro Glu Leu Gly Asn
    530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
        595                 600                 605

Thr Thr Ala Ile Leu Asp Asp Ser Trp Gln
    610                 615

<210> SEQ ID NO 12
<211> LENGTH: 574
<212> TYPE: PRT
<213> ORGANISM: Trametes cingulata

<400> SEQUENCE: 12

Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
            20                  25                  30

Ile Ala Lys Ala Gly Val Leu Ala Asn Ile Gly Pro Ser Gly Ser Lys
        35                  40                  45
```

```
Ser Asn Gly Ala Lys Ala Gly Ile Val Ile Ala Ser Pro Ser Thr Ser
    50              55                  60

Asn Pro Asn Tyr Leu Tyr Thr Trp Thr Arg Asp Ser Ser Leu Val Phe
65              70                  75                  80

Lys Ala Leu Ile Asp Gln Phe Thr Thr Gly Glu Asp Thr Ser Leu Arg
                85                  90                  95

Thr Leu Ile Asp Glu Phe Thr Ser Ala Glu Ala Ile Leu Gln Gln Val
            100                 105                 110

Pro Asn Pro Ser Gly Thr Val Ser Thr Gly Leu Gly Glu Pro Lys
            115                 120                 125

Phe Asn Ile Asp Glu Thr Ala Phe Thr Asp Ala Trp Gly Arg Pro Gln
130                 135                 140

Arg Asp Gly Pro Ala Leu Arg Ala Thr Ala Ile Ile Thr Tyr Ala Asn
145                 150                 155                 160

Trp Leu Leu Asp Asn Lys Asn Thr Thr Tyr Val Thr Asn Thr Leu Trp
                165                 170                 175

Pro Ile Ile Lys Leu Asp Leu Asp Tyr Val Ala Ser Asn Trp Asn Gln
                180                 185                 190

Ser Thr Phe Asp Leu Trp Glu Glu Ile Asn Ser Ser Ser Phe Phe Thr
        195                 200                 205

Thr Ala Val Gln His Arg Ala Leu Arg Glu Gly Ala Thr Phe Ala Asn
        210                 215                 220

Arg Ile Gly Gln Thr Ser Val Val Ser Gly Tyr Thr Thr Gln Ala Asn
225                 230                 235                 240

Asn Leu Leu Cys Phe Leu Gln Ser Tyr Trp Asn Pro Thr Gly Gly Tyr
                245                 250                 255

Ile Thr Ala Asn Thr Gly Gly Arg Ser Gly Lys Asp Ala Asn Thr
        260                 265                 270

Val Leu Thr Ser Ile His Thr Phe Asp Pro Ala Ala Gly Cys Asp Ala
        275                 280                 285

Val Thr Phe Gln Pro Cys Ser Asp Lys Ala Leu Ser Asn Leu Lys Val
        290                 295                 300

Tyr Val Asp Ala Phe Arg Ser Ile Tyr Ser Ile Asn Ser Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Ile Val Trp Asn Lys Leu Gly Ala Leu Asn Val Thr
            355                 360                 365

Ser Thr Ser Leu Pro Phe Phe Gln Gln Phe Ser Ser Gly Val Thr Val
    370                 375                 380

Gly Thr Tyr Ala Ser Ser Ser Thr Phe Lys Thr Leu Thr Ser Ala
385                 390                 395                 400

Ile Lys Thr Phe Ala Asp Gly Phe Leu Ala Val Asn Ala Lys Tyr Thr
                405                 410                 415

Pro Ser Asn Gly Gly Leu Ala Glu Gln Tyr Ser Arg Ser Asn Gly Ser
            420                 425                 430

Pro Val Ser Ala Val Asp Leu Thr Trp Ser Tyr Ala Ala Ala Leu Thr
            435                 440                 445

Ser Phe Ala Ala Arg Ser Gly Lys Thr Tyr Ala Ser Trp Gly Ala Ala
    450                 455                 460

Gly Leu Thr Val Pro Thr Thr Cys Ser Gly Ser Gly Gly Ala Gly Thr
```

```
            465                 470                 475                 480
Val Ala Val Thr Phe Asn Val Gln Ala Thr Thr Val Phe Gly Glu Asn
                    485                 490                 495

Ile Tyr Ile Thr Gly Ser Val Pro Ala Leu Gln Asn Trp Ser Pro Asp
                500                 505                 510

Asn Ala Leu Ile Leu Ser Ala Ala Asn Tyr Pro Thr Trp Ser Ile Thr
                515                 520                 525

Val Asn Leu Pro Ala Ser Thr Thr Ile Glu Tyr Lys Tyr Ile Arg Lys
            530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
                565                 570

<210> SEQ ID NO 13
<211> LENGTH: 583
<212> TYPE: PRT
<213> ORGANISM: Rhizomucor pusillus

<400> SEQUENCE: 13

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
            35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270
```

```
Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
        290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Thr Ser Lys Thr Thr Ala Thr Ala
450                 455                 460

Ser Lys Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 14
<211> LENGTH: 661
<212> TYPE: PRT
<213> ORGANISM: Trichoderma reesei

<400> SEQUENCE: 14

Leu Tyr Ile Asn Gly Ser Val Ile Ala Pro Cys Asp Ser Pro Ile Tyr
1               5                   10                  15

Cys His Gly Asp Ile Leu Arg Glu Ile Glu Leu Ala His Pro Phe Ser
            20                  25                  30

Asp Ser Lys Thr Phe Val Asp Met Pro Ala Lys Arg Pro Leu Ser Glu
        35                  40                  45

Ile Gln Thr Ala Phe Ala Asn Leu Pro Lys Pro Leu Arg Asn Asp Ser
    50                  55                  60
```

Ser Leu Gln Thr Phe Leu Ala Ser Tyr Phe Ala Asp Ala Gly Gly Glu
 65                  70                  75                  80

Leu Ile Gln Val Pro Arg Ala Asn Leu Thr Thr Asn Pro Thr Phe Leu
                 85                  90                  95

Ser Lys Ile Asn Asp Thr Val Ile Glu Gln Phe Val Thr Gln Val Ile
            100                 105                 110

Asp Ile Trp Pro Asp Leu Thr Arg Arg Tyr Ala Gly Asp Ala Ala Val
        115                 120                 125

Lys Asn Cys Ser Ser Cys Pro Asn Ser Phe Ile Pro Val Asn Arg Thr
130                 135                 140

Phe Val Val Ala Gly Gly Arg Phe Arg Glu Pro Tyr Tyr Trp Asp Ser
145                 150                 155                 160

Tyr Trp Ile Val Glu Gly Leu Leu Arg Thr Gly Gly Ala Phe Val Gly
                165                 170                 175

Ile Ala Arg Asn Thr Ile Asp Asn Phe Leu Asp Phe Ile Glu Arg Phe
            180                 185                 190

Gly Phe Val Pro Asn Gly Ala Arg Leu Tyr Tyr Leu Asn Arg Ser Gln
        195                 200                 205

Pro Pro Leu Leu Ser Arg Met Val Lys Val Tyr Ile Asp His Thr Asn
210                 215                 220

Asp Thr Ala Ile Leu Arg Arg Ala Leu Pro Leu Leu Val Lys Glu His
225                 230                 235                 240

Glu Phe Trp Thr Arg Asn Arg Thr Val Asp Val Arg Val Asn Asn Lys
                245                 250                 255

Thr Tyr Val Leu Asn Gln Tyr Ala Val Gln Asn Thr Gln Pro Arg Pro
            260                 265                 270

Glu Ser Phe Arg Glu Asp Phe Gln Thr Ala Asn Asn Arg Ser Tyr Tyr
        275                 280                 285

Ala Ala Ser Gly Ile Ile Tyr Pro Ala Thr Lys Pro Leu Asn Glu Ser
290                 295                 300

Gln Ile Glu Glu Leu Tyr Ala Asn Leu Ala Ser Gly Ala Glu Ser Gly
305                 310                 315                 320

Asn Asp Tyr Thr Ala Arg Trp Leu Ala Asp Pro Ser Asp Ala Met Arg
                325                 330                 335

Asp Val Tyr Phe Pro Leu Arg Ser Leu Asn Asn Lys Asp Ile Val Pro
            340                 345                 350

Val Asp Leu Asn Ser Ile Leu Tyr Gly Asn Glu Leu Ala Ile Ala Gln
        355                 360                 365

Phe Tyr Asn Gln Thr Gly Asn Thr Thr Ala Ala Arg Glu Trp Ser Ser
        370                 375                 380

Leu Ala Ala Asn Arg Ser Ala Ser Ile Gln Ala Val Phe Trp Asn Glu
385                 390                 395                 400

Thr Leu Phe Ser Tyr Phe Asp Tyr Asn Leu Thr Ser Ser Ser Gln Asn
                405                 410                 415

Ile Tyr Val Pro Leu Asp Lys Asp Ala Val Ala Leu Asp Arg Gln Thr
            420                 425                 430

Ala Pro Pro Gly Lys Gln Val Leu Phe His Val Gly Gln Phe Tyr Pro
        435                 440                 445

Phe Trp Thr Gly Ala Ala Pro Glu Tyr Leu Arg Asn Asn Pro Phe Ala
        450                 455                 460

Val Thr Arg Ile Phe Asp Arg Val Lys Ser Tyr Leu Asp Thr Arg Pro
465                 470                 475                 480

```
Gly Gly Ile Pro Ala Ser Asn Val Asn Thr Gly Gln Gln Trp Asp Gln
                485                 490                 495

Pro Asn Val Trp Pro Pro His Met His Ile Leu Met Glu Ser Leu Asn
            500                 505                 510

Ser Val Pro Ala Thr Phe Ser Glu Ala Asp Pro Ala Tyr Gln Asp Val
        515                 520                 525

Arg Asn Leu Ser Leu Arg Leu Gly Gln Arg Tyr Leu Asp Phe Thr Phe
    530                 535                 540

Cys Thr Trp Arg Ala Thr Gly Gly Ser Thr Ser Glu Thr Pro Lys Leu
545                 550                 555                 560

Gln Gly Leu Thr Asp Gln Asp Val Gly Ile Met Phe Glu Lys Tyr Asn
                565                 570                 575

Asp Asn Ser Thr Asn Ala Ala Gly Gly Gly Glu Tyr Gln Val Val
            580                 585                 590

Glu Gly Phe Gly Trp Thr Asn Gly Val Leu Leu Trp Thr Ala Asp Thr
        595                 600                 605

Phe Gly Ser Gln Leu Lys Arg Pro Gln Cys Gly Asn Ile Met Ala Gly
    610                 615                 620

His Pro Ala Pro Ser Lys Arg Ser Ala Val Gln Leu Asp Met Trp Asp
625                 630                 635                 640

Ala Ser Arg Val Lys Lys Phe Gly Arg Arg Ala Glu Gly Arg Met Gly
                645                 650                 655

Thr Leu His Ala Trp
            660

<210> SEQ ID NO 15
<211> LENGTH: 862
<212> TYPE: PRT
<213> ORGANISM: Bacillus sp.
<220> FEATURE:
<221> NAME/KEY: SIGNAL
<222> LOCATION: (1)..(33)

<400> SEQUENCE: 15

Met Ser Leu Ile Arg Ser Arg Tyr Asn His Phe Val Ile Leu Phe Thr
1               5                   10                  15

Val Ala Ile Met Phe Leu Thr Val Cys Phe Pro Ala Tyr Lys Ala Leu
                20                  25                  30

Ala Asp Ser Thr Ser Thr Glu Val Ile Val His Tyr His Arg Phe Asp
            35                  40                  45

Ser Asn Tyr Ala Asn Trp Asp Leu Trp Met Trp Pro Tyr Gln Pro Val
        50                  55                  60

Asn Gly Asn Gly Ala Ala Tyr Glu Phe Ser Gly Lys Asp Asp Phe Gly
65                  70                  75                  80

Val Lys Ala Asp Val Gln Val Pro Gly Asp Asp Thr Gln Val Gly Leu
                85                  90                  95

Ile Val Arg Thr Asn Asp Trp Ser Gln Lys Asn Thr Ser Asp Asp Leu
            100                 105                 110

His Ile Asp Leu Thr Lys Gly His Glu Ile Trp Ile Val Gln Gly Asp
        115                 120                 125

Pro Asn Ile Tyr Tyr Asn Leu Ser Asp Ala Gln Ala Ala Ala Thr Pro
    130                 135                 140

Lys Val Ser Asn Ala Tyr Leu Asp Asn Glu Lys Thr Val Leu Ala Lys
145                 150                 155                 160

Leu Thr Asn Pro Met Thr Leu Ser Asp Gly Ser Ser Gly Phe Thr Val
                165                 170                 175
```

```
Thr Asp Lys Thr Thr Gly Glu Gln Ile Pro Val Thr Ala Ala Thr Asn
            180                 185                 190

Ala Asn Ser Ala Ser Ser Glu Gln Thr Asp Leu Val Gln Leu Thr
        195                 200                 205

Leu Ala Ser Ala Pro Asp Val Ser His Thr Ile Gln Val Gly Ala Ala
        210                 215                 220

Gly Tyr Glu Ala Val Asn Leu Ile Pro Arg Asn Val Leu Asn Leu Pro
225                 230                 235                 240

Arg Tyr Tyr Tyr Ser Gly Asn Asp Leu Gly Asn Val Tyr Ser Asn Lys
                245                 250                 255

Ala Thr Ala Phe Arg Val Trp Ala Pro Thr Ala Ser Asp Val Gln Leu
            260                 265                 270

Leu Leu Tyr Asn Ser Glu Thr Gly Pro Val Thr Lys Gln Leu Glu Met
        275                 280                 285

Gln Lys Ser Asp Asn Gly Thr Trp Lys Leu Lys Val Pro Gly Asn Leu
        290                 295                 300

Lys Asn Trp Tyr Tyr Leu Tyr Gln Val Thr Val Asn Gly Lys Thr Gln
305                 310                 315                 320

Thr Ala Val Asp Pro Tyr Val Arg Ala Ile Ser Val Asn Ala Thr Arg
                325                 330                 335

Gly Met Ile Val Asp Leu Glu Asp Thr Asn Pro Pro Gly Trp Lys Glu
            340                 345                 350

Asp His Gln Gln Thr Pro Ala Asn Pro Val Asp Glu Val Ile Tyr Glu
        355                 360                 365

Val His Val Arg Asp Phe Ser Ile Asp Ala Asn Ser Gly Met Lys Asn
        370                 375                 380

Lys Gly Lys Tyr Leu Ala Phe Thr Glu His Gly Thr Lys Gly Pro Asp
385                 390                 395                 400

Asn Val Lys Thr Gly Ile Asp Ser Leu Lys Glu Leu Gly Ile Asn Ala
                405                 410                 415

Val Gln Leu Gln Pro Ile Glu Glu Phe Asn Ser Ile Asp Glu Thr Gln
            420                 425                 430

Pro Asn Met Tyr Asn Trp Gly Tyr Asp Pro Arg Asn Tyr Asn Val Pro
        435                 440                 445

Glu Gly Ala Tyr Ala Thr Thr Pro Glu Gly Thr Ala Arg Ile Thr Gln
        450                 455                 460

Leu Lys Gln Leu Ile Gln Ser Ile His Lys Asp Arg Ile Ala Ile Asn
465                 470                 475                 480

Met Asp Val Val Tyr Asn His Thr Phe Asn Val Gly Val Ser Asp Phe
                485                 490                 495

Asp Lys Ile Val Pro Gln Tyr Tyr Arg Thr Asp Ser Ala Gly Asn
            500                 505                 510

Tyr Thr Asn Gly Ser Gly Val Gly Asn Glu Ile Ala Thr Glu Arg Pro
        515                 520                 525

Met Val Gln Lys Phe Val Leu Asp Ser Val Lys Tyr Trp Val Lys Glu
        530                 535                 540

Tyr His Ile Asp Gly Phe Arg Phe Asp Leu Met Ala Leu Leu Gly Lys
545                 550                 555                 560

Asp Thr Met Ala Lys Ile Ser Lys Glu Leu His Ala Ile Asn Pro Gly
                565                 570                 575

Ile Val Leu Tyr Gly Glu Pro Trp Thr Gly Thr Gly Leu Ser
            580                 585                 590
```

```
Ser Asp Gln Leu Val Thr Lys Gly Gln Gln Lys Gly Leu Gly Ile Gly
        595                 600                 605

Val Phe Asn Asp Asn Ile Arg Asn Gly Leu Asp Gly Asn Val Phe Asp
610                 615                 620

Lys Ser Ala Gln Gly Phe Ala Thr Gly Asp Pro Asn Gln Val Asn Val
625                 630                 635                 640

Ile Lys Asn Gly Val Met Gly Ser Ile Ser Asp Phe Thr Ser Ala Pro
                645                 650                 655

Ser Glu Thr Ile Asn Tyr Val Thr Ser His Asp Asn Met Thr Leu Trp
                660                 665                 670

Asp Lys Ile Ser Ala Ser Asn Pro Asn Asp Thr Gln Ala Asp Arg Ile
            675                 680                 685

Lys Met Asp Glu Leu Ala Gln Ala Val Val Phe Thr Ser Gln Gly Val
        690                 695                 700

Pro Phe Met Gln Gly Gly Glu Glu Met Leu Arg Thr Lys Gly Gly Asn
705                 710                 715                 720

Asp Asn Ser Tyr Asn Ala Gly Asp Ser Val Asn Gln Phe Asp Trp Ser
                725                 730                 735

Arg Lys Ala Gln Phe Glu Asn Val Phe Asp Tyr Tyr Ser Trp Leu Ile
            740                 745                 750

His Leu Arg Asp Asn His Pro Ala Phe Arg Met Thr Thr Ala Asp Gln
        755                 760                 765

Ile Lys Gln Asn Leu Thr Phe Leu Asp Ser Pro Thr Asn Thr Val Ala
    770                 775                 780

Phe Glu Leu Lys Asn His Ala Asn His Asp Lys Trp Lys Asn Ile Ile
785                 790                 795                 800

Val Met Tyr Asn Pro Asn Lys Thr Ala Gln Thr Leu Thr Leu Pro Ser
                805                 810                 815

Gly Asn Trp Thr Ile Val Gly Leu Gly Asn Gln Val Gly Glu Lys Ser
            820                 825                 830

Leu Gly His Val Asn Gly Thr Val Glu Val Pro Ala Leu Ser Thr Ile
        835                 840                 845

Ile Leu His Gln Gly Thr Ser Glu Asp Val Ile Asp Gln Asn
    850                 855                 860

<210> SEQ ID NO 16
<211> LENGTH: 616
<212> TYPE: PRT
<213> ORGANISM: Penicillium oxalicum

<400> SEQUENCE: 16

Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Asn Leu Thr Pro
                20                  25                  30

Phe Ile His Lys Glu Gly Glu Arg Ser Leu Gln Gly Ile Leu Asp Asn
                35                  40                  45

Leu Gly Gly Arg Gly Lys Lys Thr Pro Gly Thr Ala Ala Gly Leu Phe
        50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
                100                 105                 110
```

```
Arg Asp Tyr Val Ser Ser Gln Ala Ile Leu Gln Ser Val Ser Asn Pro
        115                 120                 125

Ser Gly Thr Leu Lys Asp Gly Ser Gly Leu Gly Glu Pro Lys Phe Glu
    130                 135                 140

Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
                165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
        195                 200                 205

Phe Asp Leu Trp Glu Glu Val Asp Gly Ser Ser Phe Phe Thr Ile Ala
    210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Gln Ile Leu Cys
                245                 250                 255

Phe Leu Gln Ser Phe Trp Asn Gly Lys Tyr Ile Thr Ser Asn Ile Asn
        260                 265                 270

Thr Gln Ala Ser Arg Ser Gly Ile Asp Leu Asp Ser Val Leu Gly Ser
    275                 280                 285

Ile His Thr Phe Asp Pro Glu Ala Ala Cys Asp Ala Thr Phe Gln
        290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
        355                 360                 365

Tyr Gln Trp Asp Arg Leu Gly Lys Leu Glu Val Ser Glu Thr Ser Leu
    370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
            420                 425                 430

Ser Leu Ala Glu Gln Tyr Asp Arg Asn Thr Ala Ala Pro Leu Ser Ala
        435                 440                 445

Asn Asp Leu Thr Trp Ser Phe Ala Ser Phe Leu Thr Ala Thr Gln Arg
    450                 455                 460

Arg Asp Ala Val Val Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Tyr Gly Glu
        515                 520                 525
```

-continued

```
Asn Val Phe Met Ser Gly Asn Ile Thr Ala Leu Gly Asn Trp Asp Ala
            530                 535                 540

Lys Lys Gly Phe Pro Leu Thr Ala Asn Leu Tyr Thr Gln Asp Gln Asn
545                 550                 555                 560

Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
                580                 585                 590

Gly Pro Asn Arg Val Phe Val Ala Pro Thr Gly Cys Pro Val Gln Pro
            595                 600                 605

His Ser Asn Asp Val Trp Gln Phe
    610                 615
```

<210> SEQ ID NO 17
<211> LENGTH: 573
<212> TYPE: PRT
<213> ORGANISM: Pycnoporus sanguineus
<220> FEATURE:
<221> NAME/KEY: SIGNAL
<222> LOCATION: (1)..(18)

<400> SEQUENCE: 17

```
Met Arg Phe Thr Leu Leu Ala Ser Leu Ile Gly Leu Ala Val Gly Ala
1               5                   10                  15

Phe Ala Gln Ser Ser Ala Val Asp Ala Tyr Val Ala Ser Glu Ser Pro
            20                  25                  30

Ile Ala Lys Gln Gly Val Leu Asn Asn Ile Gly Pro Asn Gly Ser Lys
        35                  40                  45

Ala His Gly Ala Lys Ala Gly Ile Val Val Ala Ser Pro Ser Thr Glu
    50                  55                  60

Asn Pro Asp Tyr Leu Tyr Thr Trp Thr Arg Asp Ser Ser Leu Val Phe
65                  70                  75                  80

Lys Leu Leu Ile Asp Gln Phe Thr Ser Gly Asp Asp Thr Ser Leu Arg
                85                  90                  95

Gly Leu Ile Asp Asp Phe Thr Ser Ala Glu Ala Ile Leu Gln Gln Val
            100                 105                 110

Ser Asn Pro Ser Gly Thr Val Ser Thr Gly Gly Leu Gly Glu Pro Lys
        115                 120                 125

Phe Asn Ile Asp Glu Thr Ala Phe Thr Gly Ala Trp Gly Arg Pro Gln
    130                 135                 140

Arg Asp Gly Pro Ala Leu Arg Ala Thr Ser Ile Ile Arg Tyr Ala Asn
145                 150                 155                 160

Trp Leu Leu Asp Asn Gly Asn Thr Thr Tyr Val Ser Asn Thr Leu Trp
                165                 170                 175

Pro Val Ile Gln Leu Asp Leu Asp Tyr Val Ala Asp Asn Trp Asn Gln
            180                 185                 190

Ser Thr Phe Asp Leu Trp Glu Glu Val Asp Ser Ser Phe Phe Thr
        195                 200                 205

Thr Ala Val Gln His Arg Ala Leu Arg Glu Gly Ala Thr Phe Ala Ser
    210                 215                 220

Arg Ile Gly Gln Ser Ser Val Val Ser Gly Tyr Thr Thr Gln Ala Asp
225                 230                 235                 240

Asn Leu Leu Cys Phe Leu Gln Ser Tyr Trp Asn Pro Ser Gly Gly Tyr
                245                 250                 255

Val Thr Ala Asn Thr Gly Gly Gly Arg Ser Gly Lys Asp Ser Asn Thr
            260                 265                 270
```

```
Val Leu Thr Ser Ile His Thr Phe Asp Pro Ala Ala Gly Cys Asp Ala
            275                 280                 285

Ala Thr Phe Gln Pro Cys Ser Asp Lys Ala Leu Ser Asn Leu Lys Val
        290                 295                 300

Tyr Val Asp Ala Phe Arg Ser Ile Tyr Thr Ile Asn Asn Gly Ile Ala
305                 310                 315                 320

Ser Asn Ala Ala Val Ala Thr Gly Arg Tyr Pro Glu Asp Ser Tyr Met
                325                 330                 335

Gly Gly Asn Pro Trp Tyr Leu Thr Thr Ser Ala Val Ala Glu Gln Leu
            340                 345                 350

Tyr Asp Ala Leu Tyr Val Trp Asp Gln Leu Gly Gly Leu Asn Val Thr
        355                 360                 365

Ser Thr Ser Leu Ala Phe Phe Gln Gln Phe Ala Ser Gly Leu Ser Thr
370                 375                 380

Gly Thr Tyr Ser Ala Ser Ser Thr Tyr Ala Thr Leu Thr Ser Ala
385                 390                 395                 400

Ile Arg Ser Phe Ala Asp Gly Phe Leu Ala Ile Asn Ala Lys Tyr Thr
                405                 410                 415

Pro Ala Asp Gly Gly Leu Ala Glu Gln Tyr Ser Arg Asn Asp Gly Thr
            420                 425                 430

Pro Leu Ser Ala Val Asp Leu Thr Trp Ser Tyr Ala Ala Ala Leu Thr
        435                 440                 445

Ala Phe Ala Ala Arg Glu Gly Lys Thr Tyr Gly Ser Trp Gly Ala Ala
450                 455                 460

Gly Leu Thr Val Pro Ala Ser Cys Ser Gly Gly Gly Ala Thr Val
465                 470                 475                 480

Ala Val Thr Phe Asn Val Gln Ala Thr Val Phe Gly Glu Asn Ile
                485                 490                 495

Tyr Ile Thr Gly Ser Val Ala Ala Leu Gln Asn Trp Ser Pro Asp Asn
            500                 505                 510

Ala Leu Ile Leu Ser Ala Ala Asn Tyr Pro Thr Trp Ser Ile Thr Val
        515                 520                 525

Asn Leu Pro Ala Asn Thr Val Val Gln Tyr Lys Tyr Ile Arg Lys Phe
530                 535                 540

Asn Gly Gln Val Thr Trp Glu Ser Asp Pro Asn Asn Gln Ile Thr Thr
545                 550                 555                 560

Pro Ser Gly Gly Ser Phe Thr Gln Asn Asp Val Trp Arg
                565                 570

<210> SEQ ID NO 18
<211> LENGTH: 559
<212> TYPE: PRT
<213> ORGANISM: Gloephyllum trabeum

<400> SEQUENCE: 18

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
```

-continued

```
                65                  70                  75                  80
Ile Asp Ser Phe Val Ile Ala Glu Ala Asn Ile Gln Gln Val Ser Asn
                    85                  90                  95

Pro Ser Gly Thr Leu Thr Thr Gly Gly Leu Gly Glu Pro Lys Phe Asn
                100                 105                 110

Val Asp Glu Thr Ala Phe Thr Gly Ala Trp Gly Arg Pro Gln Arg Asp
                115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Phe Phe Thr Thr Ala
                180                 185                 190

Val Gln His Arg Ala Leu Arg Glu Gly Ala Ala Phe Ala Thr Lys Ile
                195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Ile Ala Ser Asn
    290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
                340                 345                 350

Ser Leu Pro Phe Phe Gln Gln Phe Ser Ser Ser Val Thr Ala Gly Thr
                355                 360                 365

Tyr Ala Ser Ser Ser Thr Thr Tyr Thr Thr Leu Thr Ser Ala Ile Lys
    370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Val Gly Leu
                435                 440                 445

Thr Val Pro Thr Ser Cys Ser Ser Asn Ser Gly Gly Gly Gly Gly Ser
    450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495
```

```
Asp Asn Ala Leu Leu Leu Ser Ser Ala Asn Tyr Pro Thr Trp Ser Ile
            500             505             510
Thr Val Asn Leu Pro Ala Ser Thr Ala Ile Gln Tyr Lys Tyr Ile Arg
        515             520             525
Lys Asn Asn Gly Ala Val Thr Trp Glu Ser Asp Pro Asn Asn Ser Ile
        530             535             540
Thr Thr Pro Ala Ser Gly Ser Val Thr Glu Asn Asp Thr Trp Arg
545             550             555
```

PROCESSES OF PRODUCING ETHANOL USING A FERMENTING ORGANISM

CROSS-REFERENCE TO RELATED APPLICATIONS

This application is a 35 U.S.C. 371 national application of PCT/US2016/019874, filed Feb. 26, 2016, which claims priority benefit of U.S. provisional application Ser. No. 62/121,925, filed on Feb. 27, 2015. The contents of these applications are fully incorporated herein by reference.

REFERENCE TO A SEQUENCE LISTING

This application contains a Sequence Listing in computer readable form, which is incorporated herein by reference.

REFERENCE TO A DEPOSIT OF BIOLOGICAL MATERIAL

This application contains a reference to a deposit of biological material, which is incorporated herein by reference.

TECHNICAL FIELD

The present invention relates to improved raw starch hydrolysis processes of producing ethanol from starch-containing materials using a fermenting organism providing an ethanol yield boost and lower glycerol production compared to the current industry standard yeast ETHANOL RED™ under the same fermentation conditions. The invention also relates to *Saccharomyces* yeast strains having improved properties in raw starch hydrolysis processes and compositions comprising a *Saccharomyces* yeast strain of the invention and a naturally occurring and/or a non-naturally occurring component.

BACKGROUND ART

Processes of producing ethanol from starch-containing material are well-known in the art and used commercially today. The production of ethanol as a bio-fuel has become a major industry, with in excess of 21 billion gallons of ethanol being produced worldwide in 2012.

When producing ethanol, starch is conventionally converted into dextrins using a liquefying enzyme (e.g., *Bacillus* alpha-amylase) at temperatures above the initial gelatinization temperature of starch. The generated dextrins are hydrolyzed into sugars using a saccharifying enzyme (e.g., glucoamylase) and fermented into the desired fermentation product using a fermenting organism such as a yeast strain derived from *Saccharomyces cerevisiae*. Typically hydrolysis and fermentation are done in a simultaneous saccharification and fermentation (SSF) step.

Another type of process is also used commercially today. Starch is converted into sugars by enzymes at temperatures below the initial gelatinization temperature of the starch in question and converted into ethanol by yeast, typically derived from *Saccharomyces cerevisiae*. This type of process is referred to as a raw starch hydrolysis (RSH) process, or alternatively a "one-step process" or "no cook" process.

Yeast which are used for production of ethanol for use as fuel, such as in the corn ethanol industry, require several characteristics to ensure cost effective production of the ethanol. These characteristics include ethanol tolerance, low by-product yield, rapid fermentation, and the ability to limit the amount of residual sugars remaining in the ferment. Such characteristics have a marked effect on the viability of the industrial process.

Yeast of the genus *Saccharomyces* exhibit many of the characteristics required for production of ethanol. In particular, strains of *Saccharomyces cerevisiae* are widely used for the production of ethanol in the fuel ethanol industry. Strains of *Saccharomyces cerevisiae* that are widely used in the fuel ethanol industry have the ability to produce high yields of ethanol under fermentation conditions found in, for example, the fermentation of corn mash. An example of such a strain is the yeast, used in the commercially available ethanol yeast product, sold under the trade named "ETHANOL RED™" and is available from Fermentis (A Lesaffre Division).

Strains of *Saccharomyces cerevisiae* are used in the fuel ethanol industry to ferment sugars such as glucose, fructose, sucrose and maltose to produce ethanol via the glycolytic pathway. These sugars are obtained from sources such as corn and other grains, sugar juice, molasses, grape juice, fruit juices, and starchy root vegetables and may include the breakdown of cellulosic material into glucose.

Although strains of *Saccharomyces cerevisiae* currently used in the fuel ethanol industry are well suited to ethanol production, there is an increasing need for improvements in the efficiency of ethanol production owing to the increased demand for ethanol as a fuel, and the increased availability of starch in new strains of corn.

There is therefore a need for new strains of *Saccharomyces* capable of improving the efficiency of ethanol production in industrial scale fermentation.

Further, despite significant improvement of ethanol production processes over the past decade there is still a desire and need for providing further improved processes of producing ethanol from starch-containing material that, e.g., can provide a higher ethanol yield.

SUMMARY OF THE INVENTION

The invention concerns improved raw starch hydrolysis processes for producing ethanol using a fermenting organism and yeast strains suitable for use in processes and methods of the invention.

More specifically in a first aspect the invention relates to processes of producing ethanol from starch-containing material, such as granular starch, comprising:
  (i) saccharifying a starch-containing material at a temperature below the initial gelatinization temperature; and
  (ii) fermenting using a fermentation organism;
  wherein
    saccharification and/or fermentation is done in the presence of the following enzymes: glucoamylase and alpha-amylase, and optionally protease; and
    the fermenting organism is a *Saccharomyces* yeast strain providing:
      an ethanol yield boost compared to ETHANOL RED™;
      lower glycerol production compared to ETHANOL RED™;
    under the same fermentation conditions.

In a preferred embodiment the fermenting organism used in a process of the invention is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia). In an embodiment the fermenting organism is a derivative of *Saccharomyces cerevisiae* MBG4911, MBG4913 or MBG4914 having the defining characteristics (i.e., high ethanol yield boost and/or low glycerol production) of one or more of these *Saccharomyces cerevisiae* strains.

A raw starch hydrolysis process of the invention results in one or more, such as all, of the following improvements compared to a corresponding process carried out under the same conditions using ETHANOL RED™ ("ER") as the fermenting organism:
higher ethanol yield boost;
lower glycerol production.

Examples of suitable enzymes used, especially glucoamylases, alpha-amylases, proteases, cellulolytic enzyme compositions etc are described in the "Enzymes And Enzyme Blends Used In A Process Of The Invention" section below.

In a preferred embodiment the following enzymes are present and/or added in saccharification and/or fermentation: *Trametes cingulata* glucoamylase, preferably the one shown in SEQ ID NO: 12 herein and an alpha-amylase. In a preferred embodiment the alpha-amylase is a *Rhizomucor pusillus* alpha-amylase, preferably the *Rhizomucor pusillus* alpha-amylase with a linker and starch-binding domain (SBD), in particular the *Rhizomucor pusillus* alpha-amylase with *Aspergillus niger* glucoamylase linker and starch-binding domain shown in SEQ ID NO: 13 herein.

In a preferred embodiment the following enzymes are present and/or added in saccharification and/or fermentation: *Gloeophyllum trabeum* glucoamylase, preferably the one shown in SEQ ID NO: 18 herein, especially one further having one or more of the following substitutions: S95P, A121P, especially S95P+A121P and an alpha-amylase. In a preferred embodiment the alpha-amylase is derived from *Rhizomucor pusillus*, preferably *Rhizomucor pusillus* alpha-amylase with a linker and starch-binding domain (SBD), in particular the *Rhizomucor pusillus* alpha-amylase with an *Aspergillus niger* glucoamylase linker and starch-binding domain (SBD) disclosed as V039 in Table 5 in WO 2006/069290 or SEQ ID NO: 13 herein.

In another preferred embodiment of the process of the invention the following enzymes are present and/or added in saccharification and/or fermentation: *Gloeophyllum trabeum* glucoamylase, preferably the one shown in SEQ ID NO: 18 herein, preferably one further having one or more of the following substitutions: S95P, A121P, especially S95P+A121P and an alpha-amylase. The alpha-amylase may be derived from *Rhizomucor pusillus*, preferably *Rhizomucor pusillus* alpha-amylase with a linker and starch-binding domain (SBD), in particular the *Rhizomucor pusillus* alpha-amylase with *Aspergillus niger* glucoamylase linker and starch-binding domain (SBD) shown in SEQ ID NO: 13 herein, preferably one further having one or more of the following substitutions: G128D, D143N, especially G128D+143N.

In another preferred embodiment the following enzymes are present and/or added in saccharification and/or fermentation: *Pycnoporus sanguineus* glucoamylase, preferably the one shown in SEQ ID NO: 17 herein and an alpha-amylase. In a preferred embodiment the alpha-amylase is derived from *Rhizomucor pusillus*, preferably with a linker and starch-binding domain (SBD), in particular the *Rhizomucor pusillus* with an *Aspergillus niger* glucoamylase linker and starch-binding domain (SBD) disclosed as V039 in Table 5 in WO 2006/069290 or SEQ ID NO: 13 herein, preferably one further having one or more of the following substitutions: G128D, D143N, especially G128D+D143N.

In an embodiment a protease is present and/or added in saccharification and/or fermentation. In a preferred embodiment the protease is a metallo protease or a serine protease. In an embodiment the metallo protease is derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In an embodiment a cellulolytic enzyme composition is present and/or added in saccharification and/or fermentation.

In a preferred embodiment the cellulolytic enzyme composition is derived from *Trichoderma reesei*, preferably further comprising *Thermoascus aurantiacus* GH61A polypeptide having cellulolytic enhancing activity (e.g., SEQ ID NO: 2 in WO 2005/074656 or SEQ ID NO: 9 herein) and *Aspergillus fumigatus* beta-glucosidase (e.g., SEQ ID NO: 2 of WO 2005/047499 or SEQ ID NO: 8 herein), or a cellulolytic enzyme composition derived from *Trichoderma reesei*, preferably further comprising *Penicillium emersonii* GH61A polypeptide, e.g., the one disclosed as SEQ ID NO: 2 in WO 2011/041397 or SEQ ID NO: 10 herein, and *Aspergillus fumigatus* beta-glucosidase, e.g., the one disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* CBH1, e.g., the one disclosed as SEQ ID NO: 6 in WO2011/057140 and SEQ ID NO: 6 herein, and *Aspergillus fumigatus* CBH II, e.g., the one disclosed as SEQ ID NO: 18 in WO 2011/057140 and as SEQ ID NO: 7 herein.

In a preferred embodiment the glucoamylase to alpha-amylase ratio is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase:mg EP alpha-amylase).

In an embodiment the glucoamylase to alpha-amylase ratio is between 100:1 and 1:2, such as between 90:1 and 1:1, such as between 80:1 and 2:1, such as between 70:1 and 3:1, such as 16:1 (determined as AGU:FAU-F).

In a preferred embodiment the total dose of glucoamylase and alpha-amylase is from 10-1,000 μg/g DS, such as from 50-500 μg/g DS, such as 75-250 μg/g DS.

In a preferred embodiment the total dose of cellulolytic enzyme composition added is from 10-500 μg/g DS, such as from 20-400 μg/g DS, such as 20-300 μg/g DS.

In an embodiment the dose of protease added is from 1-200 μg/g DS, such as from 2-100 μg/g DS, such as 3-50 μg/g DS.

In a preferred embodiment saccharification step (a) and fermentation step (b) are carried out simultaneously.

A second aspect provides a *Saccharomyces* yeast strain providing
higher ethanol yield compared to ETHANOL RED™
lower glycerol production compared to ETHANOL RED™;
under the same fermentation conditions.

In a preferred embodiment the yeast strain is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces* cerevisiae MBG4914 (deposited as V15/001461 at National Measurement Institute, Victoria, Australia). In an embodiment the yeast strain is a derivative of *Saccharomyces cerevisiae* MBG4911, MBG4913 or MBG4914 having the defining characteristics of one or more of these *Saccharomyces cerevisiae* strains.

A third aspect provides a method of producing a *Saccharomyces* strain having the defining characteristics of a strain of the invention, in particular *Saccharomyces* MBG4911, MBG4913 or MBG4914, comprising:
(a) providing: (i) a first yeast strain; and (ii) a second yeast strain, wherein the second yeast strain is a strain of the invention, in particular *Saccharomyces* MBG4911, MBG4913 or MBG4914, respectively, or a derivative thereof;
(b) culturing the first yeast strain and the second yeast strain under conditions which permit combining of DNA between the first yeast strain and the second yeast strain;
(c) screening or selecting for a derivative of a strain of the invention, in particular *Saccharomyces* MBG4911, MBG4913 or MBG4914;
(d) optionally repeating steps (b) and (c) with the screened or selected strain from step (c) as the first and/or second strain, until a derivative is obtained which exhibits the defining characteristics of a strain of the invention, in particular *Saccharomyces* MBG4911, MBG4913 or MBG4914, respectively.

A fourth aspect provides a *Saccharomyces* yeast strain produced by the method of the third aspect.

A fifth aspect provides use of a strain of the second or fourth aspect in the production of a *Saccharomyces* strain which exhibits one or more defining characteristics of a strain of the invention, in particular *Saccharomyces* MBG4911, MBG4913 or MBG4914, respectively.

A sixth aspect provides processes of using a *Saccharomyces* yeast strain of the second or fourth aspect in a process of the first aspect.

In a final aspect the invention relates to compositions comprising a *Saccharomyces* yeast strain of the invention and a naturally occurring and/or a nonenaturally occurring component. In a preferred embodiment the naturally occurring component and/or nonenaturally occurring component is one or more of the components selected from the group consisting of: surfactants, emulsifiers, gums, swelling agents, and antioxidants.

DETAILED DESCRIPTION OF THE INVENTION

The present invention relates to improved raw starch hydrolysis processes of producing ethanol from starch-containing materials using a fermenting organism providing an ethanol yield boost and lower glycerol production compared to the current industry standard yeast ETHANOL RED™ under the same fermentation conditions. A raw starch hydrolysis process is a process where starch, typically granular starch, is converted into dextrins/sugars by raw starch degrading enzymes at temperatures below the initial gelatinization temperature of the starch in question and converted into ethanol by yeast, typically *Saccharomyces cerevisiae*. This type of process is often alternatively referred to as a "one-step process" or "no cook" process. The invention also relates to *Saccharomyces* yeast strains having improved properties compared to ETHANOL RED™ (*Saccharomyces cerevisiae* yeast developed for the industrial ethanol industry).

Specifically, the invention relates to processes of ethanol production from starch-containing material, such as granular starch, comprising:
(i) saccharifying a starch-containing material at a temperature below the initial gelatinization temperature; and
(ii) fermenting using a fermentation organism;
wherein
saccharification and/or fermentation is done in the presence of the following enzymes: glucoamylase and alpha-amylase, and optionally protease; and
the fermenting organism is a *Saccharomyces* strain providing:
an ethanol yield boost compared to ETHANOL RED™;
lower glycerol production compared to ETHANOL RED™;
under the same fermentation conditions.

In an embodiment the fermenting organism can grow on xylose as a sole carbon source, e.g., determined using the Test T1.

In an embodiment the fermenting organism shows more than two-fold increase in biomass, such as more than six-fold increase in biomass, such as more than 20-fold increase in biomass determined using the Test T1 (described in the Materials & Methods" section below.

The inventors have surprisingly found that raw starch hydrolysis (RSH) processes of the invention using MBG4911, MBG4913 or MBG4914, respectively, result in higher ethanol yield compared to corresponding processes where ETHANOL RED™ ("ER") is used under the same conditions. See for instance, Example 3, table 2; and Example 4, table 5.

Raw starch hydrolysis (RSH) processes of the invention using MBG4911, MBG4913 or MBG4914, respectively, result in lower glycerol production compared to corresponding processes where ETHANOL RED™ ("ER") is used under the same conditions. See for instance, Example 3, table 3; and Example 4, table 6.

The process conditions may according to the invention may be as described in any of Examples 3 and 4.

As described in more details in Examples 3 and 4 the yeast strains are compared to ETHANOL RED™ by:
1) preparing a ground corn mash preparation having about 33-34% dry solids (DS), supplementing with 3 ppm LACTROL™ and 500 ppm urea and adjusting to pH 4.5 with 40% $H_2SO_4$.
2) rehydrating the yeast strains by weighing approximately 5 g of dried yeast into 50 ml of about 36-37° C. tap water in a flask, covering the flask, incubating in a 36-37° C. water bath for a total of 20 minutes, removing the flask, and enumerated the yeast.
3) Dosing enzymes at 0.5 AGU/g DS, added the yeast in question and ETHANOL RED™, respectively, at a pitch of 5 million cells per gram, adding water to a total volume added and fermenting at 32° C. for 88 hours.
4) Analysing for ethanol using a HPLC.

According to the invention a yeast strain of the invention has the following defining characteristics:
provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™; and/or provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™.

In a preferred embodiment of the invention the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia).

In another embodiment the fermenting organism used in a process of the invention is selected from the group of derivatives of *Saccharomyces cerevisiae* MBG 4911, MBG4913 or MBG4914 having the defining characteristics of one or more of these *Saccharomyces cerevisiae* strains.

According to the invention the yeast may be in any viable form, including crumbled, dry, including active dry and instant, compressed, cream form etc. In a preferred embodiment the *Saccharomyces cerevisiae* yeast strain used in a process of the invention is dry yeast, such as active dry yeast. In a preferred embodiment the *Saccharomyces cerevisiae* yeast strain used in a process of the invention is compressed yeast. In an embodiment the *Saccharomyces cerevisiae* yeast strain used in a process of the invention is cream yeast.

Raw Starch Hydrolysis Processes:

In processes of the invention the starch does not gelatinize as the process is carried out at temperatures below the initial gelatinization temperature of the starch in question.

The term "initial gelatinization temperature" means the lowest temperature at which starch gelatinization commences. In general, starch heated in water begins to gelatinize between about 50° C. and 75° C. The exact temperature of gelatinization depends on the specific starch and depends on the degree of cross-linking of the amylopectin. The initial gelatinization temperature can readily be determined by the skilled artisan. The initial gelatinization temperature may vary according to the plant species, to the particular variety of the plant species as well as with the growth conditions. In context of this invention the initial gelatinization temperature of a given starch-containing material may be determined as the temperature at which birefringence is lost in 5% of the starch granules using the method described by Gorinstein. S. and Lii. C., Starch/Stärke, Vol. 44 (12) pp. 461-466 (1992).

Therefore, according to the process of the invention ethanol is produced from un-gelatinized (i.e., uncooked), preferably milled grains, such as corn, or small grains such as wheat, oats, barley, rye, rice, or cereals such as sorghum. Examples of suitable starch-containing starting materials are listed in the section "Starch-Containing Materials"-section below.

In a preferred embodiment the enzymes may be added as one or more enzyme blends. According to the invention the fermentation product, i.e., ethanol, is produced without liquefying the starch-containing material. The process of the invention includes saccharifying (e.g., milled) starch-containing material, especially granular starch, below the initial gelatinization temperature, in the presence of at least a glucoamylase and an alpha-amylase and optionally a protease and/or a cellulolytic enzyme composition. The dextrins/sugars generated during saccharification can may according to the invention be simultaneously fermented into ethanol by one or more suitable fermenting organism, especially *Saccharomyces cerevisiae* MBG4911, MBG4914, and/or MBG4914 or fermenting organism(s) having properties that are about the same as that of *Saccharomyces cerevisiae* MBG4911, MBG4913 or MBG4913, especially derivatives of *Saccharomyces* strain MBG4911, MBG4913 and/or MBG4914 having the defining characteristics of said strains. See the "Fermenting Organisms"-section below.

In a preferred embodiment step (a) and step (b) are carried out simultaneously (i.e., often referred to as "simultaneous saccharification and fermentation" or "one-step fermentation"). However, step (a) and step (b) may also be carried our sequentially.

Before step (a) an aqueous slurry of starch-containing material, such as especially granular starch, having 10-55 wt.-% dry solids (DS), preferably 25-45 wt.-% dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants. A process of the invention is carried out below the initial gelatinization temperature and thus no significant viscosity increase takes place. High levels of stillage may be used, if desired. In an embodiment the aqueous slurry contains from about 1 to about 70 vol.-%, preferably 15-60% vol.-%, especially from about 30 to 50 vol.-% water and/or process waters, such as stillage (backset), scrubber water, evaporator condensate or distillate, side-stripper water from distillation, or process water from other fermentation product plants, or combinations thereof, or the like.

In an embodiment backset, or another recycled stream, is added to the slurry before step (a), or to the saccharification (step (a)), or to the simultaneous saccharification and fermentation steps (combined step (a) and step (b)).

After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolysate.

A process of the invention is conducted at a temperature below the initial gelatinization temperature, which means that the temperature at which a separate step (a) is carried out typically lies in the range between 25-75° C., such as between 30-70° C., or between 45-60° C.

In a preferred embodiment the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

In an embodiment of the invention fermentation or SSF is carried out for 30 to 150 hours, preferably 48 to 96 hours.

In an embodiment fermentation, especially SSF, is carried out so that the sugar level, such as glucose level, is kept at a low level, such as below 6 wt.-%, such as below about 3 wt.-%, such as below about 2 wt.-%, such as below about 1 wt.-%, such as below about 0.5%, or below 0.25% wt.-%, such as below about 0.1 wt.-%. Such low levels of sugar can be accomplished by simply employing adjusted quantities of enzymes and fermenting organism. A skilled person in the art can easily determine which doses/quantities of enzyme and fermenting organism, in particular MBG4911, MBG4913 and/or MBG4914, to use. The employed quantities of enzymes and fermenting organism(s) may also be selected to maintain low concentrations of maltose in the fermentation broth. For instance, the maltose level may be kept below about 0.5 wt.-%, such as below about 0.2 wt.-%.

The process of the invention may be carried out at a pH from 3 and 7, preferably from 3 to 6, or more preferably from 3.5 to 5.0.

The term "granular starch" means raw uncooked starch, i.e., starch in its natural form found in, e.g., cereal, tubers or grains. Starch is formed within plant cells as tiny granules insoluble in water. When put in cold water, the starch granules may absorb a small amount of the liquid and swell. At temperatures up to around 50° C. to 75° C. the swelling may be reversible. However, at higher temperatures an irreversible swelling called "gelatinization" begins. The granular starch may be a highly refined starch, preferably at least 90%, at least 95%, at least 97% or at least 99.5% pure, or it may be a more crude starch-containing materials comprising (e.g., milled) whole grains including non-starch fractions such as germ residues and fibers.

The raw material, such as whole grains, may be reduced in particle size, e.g., by milling, in order to open up the structure and allowing for further processing. Examples of suitable particle sizes are disclosed in U.S. Pat. No. 4,514,496 (Suntory Ltd), see e.g., claim 8, and WO2004/081193 (Broin And Associates, Inc.), see, e.g., page 5, line 28 to page 6, line 2, both references hereby incorporated by reference. Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In a preferred embodiment starch-containing material is prepared by reducing the particle size of the starch-containing material, preferably by milling, such that at least 50% of the starch-containing material has a particle size of 0.1-0.5 mm.

According to the invention the enzymes are added so that the glucoamylase is present in an amount of 0.001 to 10 AGU/g DS, preferably from 0.01 to 5 AGU/g DS, especially 0.1 to 0.5 AGU/g DS.

According to the invention the enzymes are added so that the alpha-amylase is present or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

According to the invention the enzymes are added so that the cellulolytic enzyme composition is present or added in an amount 1-10,000 micro grams EP/g DS, such as 2-5,000, such as 3 and 1,000, such as 4 and 500 micro grams EP/g DS.

According to the invention the enzymes are added so that the cellulolytic enzyme composition is present or added in an amount in the range from 0.1-100 FPU per gram total solids (TS), preferably 0.5-50 FPU per gram TS, especially 1-20 FPU per gram TS.

In an embodiment of the invention the enzymes are added so that the protease is present in an amount of 0.0001-1 mg enzyme protein per g DS, preferably 0.001 to 0.1 mg enzyme protein per g DS. Alternatively, the protease is present and/or added in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

In an embodiment of the invention the enzymes are added so that the protease is present or added in an amount in the range 1-1,000 µg EP/g DS, such as 2-500 µg EP/g DS, such as 3-250 µg EP/g DS.

In a preferred embodiment the ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase:mg EP alpha-amylase).

In an embodiment the glucoamylase to alpha-amylase ratio is between 100:1 and 1:2, such as between 90:1 and 1:1, such as between 80:1 and 2:1, such as between 70:1 and 3:1, such as 16:1 (determined as AGU:FAU-F).

In a preferred embodiment the total dose of glucoamylase and alpha-amylase is according to the invention from 10-1,000 µg/g DS, such as from 50-500 µg/g DS, such as 75-250 µg/g DS.

In a preferred embodiment the total dose of cellulolytic enzyme composition added is from 10-500 µg/g DS, such as from 20-400 µg/g DS, such as 20-300 µg/g DS.

In an embodiment the dose of protease added is from 1-200 µg/g DS, such as from 2-100 µg/g DS, such as 3-50 µg/g DS.

Starch-Containing Materials

According to the process of the invention any suitable starch-containing starting material, in particular granular starch (raw uncooked starch), may be used. The starting material is generally selected based on the desired fermentation product. Examples of starch-containing starting materials, suitable for use in processes of the present invention, include cereal, tubers or grains. Specifically the starch-containing material may be corn, wheat, barley, rye, milo, sago, cassava, tapioca, sorghum, rice, peas, beans, sweet potatoes or oats, or mixtures thereof. Contemplated are also waxy and non-waxy types of corn and barley.

In a preferred embodiment the starch-containing starting material is corn.

In a preferred embodiment the starch-containing starting material is wheat.

In a preferred embodiment the starch-containing starting material is barley.

In a preferred embodiment the starch-containing starting material is rye.

In a preferred embodiment the starch-containing starting material is milo.

In a preferred embodiment the starch-containing starting material is sago.

In a preferred embodiment the starch-containing starting material is cassava.

In a preferred embodiment the starch-containing starting material is tapioca.

In a preferred embodiment the starch-containing starting material is sorghum.

In a preferred embodiment the starch-containing starting material is rice,

In a preferred embodiment the starch-containing starting material is peas.

In a preferred embodiment the starch-containing starting material is beans.

In a preferred embodiment the starch-containing starting material is sweet potatoes.

In a preferred embodiment the starch-containing starting material is oats.

Fermenting Organisms Used in a Process of the Invention

According to invention, the fermenting organism used in a raw starch hydrolysis process of the invention is a *Saccharomyces* strain providing:

an ethanol yield boost compared to ETHANOL RED™;
lower glycerol production compared to ETHANOL RED™;

under the same fermentation conditions.

In an embodiment the fermenting organism can grow on xylose as a sole carbon source, e.g., determined using the Test T1 (described in the Materials & Methods" section below).

In an embodiment the fermenting organism shows more than two-fold increase in biomass, such as more than six-fold increase in biomass, such as more than 20-fold increase in biomass determined using the Test T1.

In an embodiment the fermenting organism used in a process of the invention provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™.

In an embodiment the fermenting organism used in a process of the invention provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™.

In a preferred embodiment of the invention the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia).

In another embodiment the fermenting organism used in a process of the invention is selected from the group of derivatives of *Saccharomyces cerevisiae* MBG 4911, MBG4913 or MBG4914, respectively, having the defining characteristics of one or more of these *Saccharomyces cerevisiae* strains.

Fermentation Medium

The term "fermentation medium" refers to the environment in which fermentation, using a fermenting organism, is carried out and which includes the fermentable substrate, that is, a carbohydrate source (e.g., glucose) that can be metabolized by the fermenting organism into a desired fermentation product, such as ethanol.

The fermentation medium may comprise nutrients and/or growth stimulator(s) for the fermenting organism. Nutrient and growth stimulators are widely used in the art of fermentation and include nitrogen sources, such as ammonia; urea, vitamins; and minerals, or combinations thereof.

Recovery

Subsequent to fermentation, the desired fermentation product (e.g., ethanol) may be separated/recovered from the fermentation medium. The slurry may be distilled to extract the desired fermentation product (i.e., ethanol). Alternatively the desired fermentation product (e.g., ethanol) may be extracted from the fermentation medium by micro or membrane filtration techniques. The fermentation product (e.g., ethanol) may also be recovered by stripping or other method well known in the art.

Enzymes and Enzyme Blends Used in a Process of the Invention

According to the invention a glucoamylase and an alpha-amylase are present and/or added in saccharification step (a) and/or fermentation step (b) (e.g., simultaneous saccharification and fermentation (SSF)). Optionally a protease and/or a cellulolytic enzyme composition is(are) also present and/or added. Other enzymes such as pullulanases, pectinases, and/or trehalases may also be present and/or added.

A non exhaustive list of suitable and specifically contemplated enzymes and enzyme combinations (e.g., blends) are described below.

In an embodiment the following enzymes are present and/or added during saccharification and/or fermentation: *Trametes* glucoamylase, preferably *Trametes cingulata* glucoamylase shown in SEQ ID NO: 12 herein and an alpha-amylase.

In an embodiment the glucoamylase is derived from *Trametes cingulata*, such as the one shown in SEQ ID NO: 12 herein, or a glucoamylase selected from the group consisting of:
(i) a glucoamylase comprising the mature polypeptide of SEQ ID NO: 12 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 12 herein.

In an embodiment the following enzymes are present and/or added during saccharification and/or fermentation: *Gloeophyllum* glucoamylase, preferably *Gloeophyllum trabeum* glucoamylase, especially the *Gloeophyllum trabeum* glucoamylase shown in SEQ ID NO: 18 herein and an alpha-amylase.

In an embodiment the glucoamylase is derived from *Gloeophyllum trabeum*, such as the one shown in SEQ ID NO: 18 herein, or a glucoamylase selected from the group consisting of:
(i) a glucoamylase comprising the mature polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.

In a preferred embodiment the *Gloeophyllum* glucoamylase, such as the *Gloeophyllum trabeum* glucoamylase shown in SEQ ID NO: 18, has one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 18 for numbering).

The alpha-amylase used in a process of the invention is typically a fungal alpha-amylase, such as an acid fungal alpha-amylase. In a preferred embodiment the alpha-amylase is derived from *Rhizomucor*, preferably a *Rhizomucor pusillus* alpha-amylase with a linker and starch-binding domain (SBD), preferably the *Rhizomucor pusillus* alpha-amylase with an *Aspergillus niger* glucoamylase linker and starch-binding domain (SBD) disclosed as V039 in Table 5 in WO 2006/069290 or SEQ ID NO: 13 herein.

In an embodiment the alpha-amylase is a *Rhizomucor* alpha-amylase or the *Rhizomucor pusillus* alpha-amylase with an *Aspergillus niger* glucoamylase linker and starch-binding domain (SBD) shown in SEQ ID NO: 13 herein, especially one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering).

In an embodiment the alpha-amylase is selected from the group consisting of:
(i) an alpha-amylase comprising the mature polypeptide of SEQ ID NO: 13 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 13 herein.

In an embodiment the following enzymes are present and/or added in saccharification and/or fermentation: the *Trametes cingulata* glucoamylase shown in SEQ ID NO: 12 herein and an alpha-amylase derived from *Rhizomucor pusillus*, preferably with a linker and starch-binding domain (SBD), in particular the *Rhizomucor pusillus* alpha-amylase with an *Aspergillus niger* glucoamylase linker and starch-binding domain (SBD) disclosed as V039 in Table 5 in WO 2006/069290 or SEQ ID NO: 13 herein.

In an embodiment the following enzymes are present and/or added in saccharification and/or fermentation: *Gloeophyllum* glucoamylase, preferably the *Gloeophyllum trabeum* glucoamylase shown in SEQ ID NO: 18 herein and an alpha-amylase derived from *Rhizomucor pusillus*, preferably with a linker and starch-binding domain (SBD), in particular the *Rhizomucor pusillus* alpha-amylase with an *Aspergillus niger* glucoamylase linker and starch-binding domain (SBD) disclosed as V039 in Table 5 in WO 2006/069290 or SEQ ID NO: 13 herein.

In another preferred embodiment the enzymes present and/or added comprises the *Gloeophyllum trabeum* glucoamylase shown in SEQ ID NO: 18 herein having one or more of the following substitutions: S95P, A121P, especially S95P+A121P (using SEQ ID NO: 13 herein for numbering) and the alpha-amylase derived from *Rhizomucor pusillus* with an *Aspergillus niger* glucoamylase linker and starch-binding domain (SBD), preferably one shown in SEQ ID NO: 13 herein, preferably one having one or more of the following substitutions: G128D, D143N, especially G128D+D143N (using SEQ ID NO: 13 for numbering).

In an embodiment the following enzymes are present and/or added in saccharification and/or fermentation: *Pycnoporus* glucoamylase, in particular the *Pycnoporus sanguineus* glucoamylase shown in SEQ ID NO: 17 and the *Rhizomucor pusillus* alpha-amylase with a linker and starch-binding domain (SBD), in particular the *Rhizomucor pusillus* alpha-amylase with an *Aspergillus niger* glucoamylase linker and starch-binding domain (SBD) shown in SEQ ID NO: 13 herein.

In an especially preferred embodiment the enzymes present and/or added in saccharification and/or fermentation comprises a *Pycnoporus* glucoamylase, such as the *Pycnoporus sanguineus* glucoamylase shown in SEQ ID NO: 17 herein and the alpha-amylase, in particular an alpha-amylase derived from *Rhizomucor pusillus* with a linker and starch-binding domain (SBD), preferably the *Rhizomucor pusillus* alpha-amylase with an *Aspergillus niger* glucoamylase linker and starch-binding domain (SBD) shown in SEQ ID NO: 13 herein, preferably having one or more of the following substitutions: G128D, D143N, especially G128D+D143N.

The enzymes present and/or added in saccharification and/or fermentation in a process of the invention include i) glucoamylase and ii) alpha-amylase; and may optionally further comprise iii) a cellulolytic enzyme composition and/or iv) a protease.

In an embodiment the protease is a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In an embodiment the protease, in particular derived from *Thermoascus aurantiacus*, is selected from the group consisting of:
(i) a protease comprising the mature polypeptide of SEQ ID NO: 3 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 3 herein.

In an especially preferred embodiment the enzymes present and/or added in saccharification and/or fermentation comprises the *Trametes cingulata* glucoamylase shown in SEQ ID NO: 12 herein and the alpha-amylase derived from *Rhizomucor pusillus* with an *Aspergillus niger* glucoamylase linker and starch-binding domain (SBD), preferably the one shown in SEQ ID NO: 13 herein, preferably having one or more of the following substitutions: G128D, D143N, especially G128D+D143N, and optionally further a cellulolytic enzyme composition derived from *Trichoderma reesei*, preferably further comprising *Thermoascus aurantiacus* GH61A polypeptide having cellulolytic enhancing activity (SEQ ID NO: 2 in WO 2005/074656 or SEQ ID NO: 9 herein) and *Aspergillus fumigatus* beta-glucosidase (SEQ ID NO: 2 of WO 2005/047499 or SEQ ID NO: 8 herein); or a cellulolytic enzyme composition derived from *Trichoderma reesei*, preferably further comprising *Penicillium emersonii* GH61A polypeptide disclosed as SEQ ID NO: 2 in WO 2011/041397 or SEQ ID NO: 10 herein and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein.

In an especially preferred embodiment the enzymes present and/or added in saccharification and/or fermentation comprises the *Gloeophyllum trabeum* glucoamylase shown in SEQ ID NO: 18 herein, preferably having one or more of the following substitutions: S95P, A121P, especially S95P+

A121P and the alpha-amylase derived from *Rhizomucor pusillus* with an *Aspergillus niger* glucoamylase linker and starch-binding domain (SBD), preferably the one shown in SEQ ID NO: 13 herein, preferably having one or more of the following substitutions: G128D, D143N, especially G128D+D143N, and optionally further a cellulolytic enzyme composition derived from *Trichoderma reesei*, preferably further comprising *Thermoascus aurantiacus* GH61A polypeptide having cellulolytic enhancing activity (SEQ ID NO: 2 in WO 2005/074656 or SEQ ID NO: 9 herein) and *Aspergillus fumigatus* beta-glucosidase (SEQ ID NO: 2 of WO 2005/047499 or SEQ ID NO: 8 herein); or a cellulolytic enzyme composition derived from *Trichoderma reesei*, preferably further comprising *Penicillium emersonii* GH61A polypeptide disclosed as SEQ ID NO: 2 in WO 2011/041397 or SEQ ID NO: 10 herein and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein.

In an especially preferred embodiment the enzymes present and/or added in saccharification and/or fermentation according to the invention comprises the *Pycnoporus sanguineus* glucoamylase shown in SEQ ID NO: 17 herein and the alpha-amylase derived from *Rhizomucor pusillus* with an *Aspergillus niger* glucoamylase linker and starch-binding domain (SBD), preferably the one shown in SEQ ID NO: 13 herein, preferably having one or more of the following substitutions: G128D, D143N, especially G128D+D143N, and optionally further a cellulolytic enzyme composition derived from *Trichoderma reesei*, preferably further comprising *Thermoascus aurantiacus* GH61A polypeptide having cellulolytic enhancing activity (SEQ ID NO: 2 in WO 2005/074656 or SEQ ID NO: 9 herein) and *Aspergillus fumigatus* beta-glucosidase (SEQ ID NO: 2 of WO 2005/047499 or SEQ ID NO: 8 herein); or a cellulolytic enzyme composition derived from *Trichoderma reesei*, preferably further comprising *Penicillium emersonii* GH61A polypeptide disclosed as SEQ ID NO: 2 in WO 2011/041397 or SEQ ID NO: 10 herein and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein.

In a preferred embodiment a cellulolytic enzyme composition is one described below in the "Cellulolytic Enzyme Compositions"-section.

The cellulolytic enzyme composition, protease or other enzymes, may be added in the process of the invention at the same time as the glucoamylase and alpha-amylase. According to the invention the enzymes, e.g., in the form of an enzyme composition, are added to the saccharification and/or fermentation, preferably simultaneous saccharification and fermentation (i.e., one-step process). It should be understood that the enzymes may also be added individually or as two, three, four or more enzyme compositions. In an embodiment the glucoamylase and alpha-amylase are added as one blend composition and the optional cellulolytic enzyme composition and/and optional protease are added separately. In another embodiment the glucoamylase, the alpha-amylase, and the cellulolytic enzyme composition are added as one enzyme composition and the optional protease is added separately. All enzymes may also in one embodiment be added as one enzyme composition comprising a glucoamylase, an alpha-amylase, a cellulolytic enzyme composition and/or a protease, and optionally other enzymes including pullulanase, trehalase and/or pectinase, such as pectin lyase or polygalacturonase.

Other enzymes may also be present. Specifically contemplated enzymes are described further below.

Glucoamylase

The glucoamylase used in a process of the invention may be of any origin, such as of bacterial or fungal origin. Fungal glucoamylases are preferred.

In an embodiment the glucoamylase may be one derived from a strain of *Trametes*, such as a strain of *Trametes cingulata* (SEQ ID NO: 12 herein); or a strain of *Pachykytospora*, such as a strain of *Pachykytospora papyracea*; or a strain of *Leucopaxillus*, such as a strain of *Leucopaxillus giganteus* (all disclosed in WO 2006/069289).

In a preferred embodiment the glucoamylase, in particular derived from a strain of *Trametes cingulata*, is selected from the group consisting of:
(i) a glucoamylase comprising the mature polypeptide of SEQ ID NO: 12 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 12 herein.

In an embodiment the glucoamylase is from a strain of *Aspergillus*, preferably *Aspergillus niger*, *Aspergillus awamori*, or *Aspergillus oryzae*; or a strain of *Trichoderma*, preferably *Trichoderma reesei*; or a strain of *Talaromyces*, preferably *Talaromyces emersonii* (SEQ ID NO: 11 herein).

In an embodiment the glucoamylase, such as one derived from a strain of *Talaromyces emersonii*, is selected from the group consisting of:
(i) a glucoamylase comprising the mature polypeptide of SEQ ID NO: 11 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 11 herein.

In another embodiment the glucoamylase is derived from a strain of *Penicillium*, such as a strain of *Penicillium oxalicum*.

In an embodiment the glucoamylase, such as one derived from a strain of *Penicillium oxalicum*, is selected from the group consisting of:
(i) a glucoamylase comprising the mature polypeptide of SEQ ID NO: 16 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

In an embodiment the glucoamylase is derived from a strain of *Gloeophyllum*, such as a strain of *Gloeophyllum sepiarium* or *Gloeophyllum trabeum*, such as one disclosed in WO 2011/068803 as any of SEQ ID NOs: 2, 4, 6, 8, 10, 12, 14 or 16. In a preferred embodiment the glucoamylase is SEQ ID NO: 2 in WO 2011/068803 or SEQ ID NO: 4 herein. In another embodiment the glucoamylase is SEQ ID NO: 18 in WO 2011/068803 (hereby incorporated by reference).

In a preferred embodiment the glucoamylase, such as one derived from a strain of *Gloeophyllum sepiarium*, is selected from the group consisting of:
(i) a glucoamylase comprising the mature polypeptide of SEQ ID NO: 4 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 4 herein.

In a further embodiment the glucoamylase is derived from a strain of the genus *Pycnoporus*, in particular a strain of *Pycnoporus sanguineus*, such as a strain described in WO 2011/066576 (SEQ ID NOs 2, 4 or 6). In a preferred embodiment the glucoamylase is the one shown in SEQ ID NO: 4 in WO 2011/066576 or SEQ ID NO: 17 herein.

In a preferred embodiment the glucoamylase, such as one derived from a strain of *Pycnoporus sanguineus*, is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

Contemplated are also glucoamylases which exhibit a high identity to any of the above-mentioned glucoamylases, e.g., at least 60%, at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

In a preferred embodiment the glucoamylase, such as one derived from a strain of *Gloeophyllum trabeum*, is selected from the group consisting of:
(i) a glucoamylase comprising the mature polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.

In a preferred embodiment the glucoamylase, such as the one derived from *Gloeophyllum trabeum*, shown in SEQ ID NO: 18 has one of the following substitutions: V59A; S95P; A121P; T119W; S95P+A121P; V59A+S95P; S95P+T119W; V59A+S95P+A121P; or S95P+T119W+A121P, especially S95P+A121P. In a preferred embodiment the *Gloeophyllum trabeum* glucoamylase shown in SEQ ID NO: 18 has one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 18 herein for numbering). All *Gloeophyllum trabeum* glucoamylase variants, especially variants in SEQ ID NO: 3, disclosed in WO 2014/177546 is hereby incorporated by reference.

A glucoamylase variant may comprise an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 18.

Alpha-Amylase

The alpha-amylase used in a process of the invention may be of any origin, such as of fungal or bacterial origin. In a preferred embodiment the alpha-amylase is an acid alpha-amylase, such as an acid fungal alpha-amylase, i.e., having a pH optimum below pH 7.

In an embodiment the alpha-amylase may be derived from a strain of the genus *Rhizomucor*, preferably a strain the *Rhizomucor pusillus*, such as the one shown in SEQ ID NO: 3 in WO 2013/006756 (see e.g., Table 1 in Example 1—hereby incorporated by reference), or the genus *Meripilus*, preferably a strain of *Meripilus giganteus*.

In a preferred embodiment the alpha-amylase is derived from a *Rhizomucor pusillus*, such as one with a linker and starch-binding domain (SBD), preferably *Aspergillus niger* glucoamylase linker and starch-binding domain (SBD), disclosed as V039 in Table 5 in WO 2006/069290 (incorporated by reference) or SEQ ID NO: 13 herein.

In a preferred embodiment the alpha-amylase is derived from a *Rhizomucor pusillus* with an *Aspergillus niger* glucoamylase linker and starch-binding domain (SBD), disclosed in WO 2013/006756 (incorporated by reference) or SEQ ID NO: 13 herein.

In an embodiment the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 herein for numbering).

In an embodiment the *Rhizomucor pusillus* alpha-amylase with an *Aspergillus niger* glucoamylase linker and starch-binding domain (SBD), is selected from the group consisting of:
(i) an alpha-amylase comprising the mature polypeptide of SEQ ID NO: 13 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 13 herein.

In a preferred embodiment the alpha-amylase is a variant of the *Rhizomucor pusillus* alpha-amylase with an *Aspergillus niger* glucoamylase linker and starch-binding domain (SBD), wherein the alpha-amylase variant comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity, but less than 100% to the mature polypeptide of SEQ ID NO: 13 herein.

In a preferred embodiment the alpha-amylase variant has one of the above mentioned substitutions, such as: G128D, Y141W, D143W or K192R.

In a preferred embodiment the alpha-amylase (using SEQ ID NO: 13 herein for numbering) has the following substitutions: Y141W+D143N.

In a preferred embodiment the alpha-amylase has the following substitutions: G128D+Y141W+D143N.

In a preferred embodiment the alpha-amylase has the following substitutions: G128D+Y141W+D143N+K192R;

In a preferred embodiment the alpha-amylase has the following substitutions: G128D+D143N (using SEQ ID NO: 13 for numbering).

A variant may comprise an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 13.

Protease

The enzymes present and/or added to saccharification and/or fermentation may optionally further include a protease. The protease may be of any origin, such as fungal or bacterial origin.

In an embodiment the protease is of fungal origin.

In an embodiment the protease is a metallo protease derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In an embodiment the protease, such as one derived from a strain of *Thermoascus aurantiacus*, is selected from the group consisting of:
(i) a protease comprising the mature polypeptide of SEQ ID NO: 3 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 3 herein.

In an embodiment the protease is of bacterial origin.

In an embodiment the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 5 herein.

In an embodiment the protease, such as one derived from *Pyrococcus furiosus*, is selected from the group consisting of:
(i) a protease comprising the mature polypeptide of SEQ ID NO: 5 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 5 herein.

Cellulolytic Enzyme Compositions

The enzymes present and/or added to saccharification and/or fermentation may optionally further include a cellulolytic enzyme composition. The cellulolytic enzyme composition may consist of or comprise one or more cellulolytic enzymes. The cellulolytic enzyme composition may be of any origin. In a preferred embodiment the cellulolytic enzyme composition comprises cellulolytic enzymes of fungal origin.

In an embodiment the cellulolytic enzyme composition is derived from a strain of *Trichoderma*, such as *Trichoderma reesei*; or a strain of *Humicola*, such as *Humicola insolens*; or a strain of *Chrysosporium*, such as *Chrysosporium lucknowense*; or a strain of *Penicillium*, such as *Penicillium decumbens*. In a preferred embodiment the cellulolytic enzyme composition is derived from a strain of *Trichoderma reesei*.

The cellulolytic enzyme composition may comprise a beta-glucosidase, a cellobiohydrolase, and an endoglucanase.

In an embodiment the cellulolytic enzyme composition comprising one or more polypeptides selected from the group consisting of:
beta-glucosidase;
cellobiohydrolase I;
cellobiohydrolase II;
or a mixture thereof.

In a preferred embodiment the cellulolytic enzyme composition further comprises a GH61 polypeptide having cellulolytic enhancing activity. Cellulolytic enhancing activity is defined and determined as described in WO 2011/041397 (incorporated by reference).

The term "GH61 polypeptide having cellulolytic enhancing activity" means a GH61 polypeptide that enhances the hydrolysis of a cellulosic material by enzymes having cellulolytic activity. For purposes of the present invention, cellulolytic enhancing activity is determined by measuring the increase in reducing sugars or the increase of the total of cellobiose and glucose from hydrolysis of a cellulosic material by cellulolytic enzyme under the following conditions: 1-50 mg of total protein/g of cellulose in PCS (Pretreated Corn Stover), wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST™1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (see SEQ ID NOs: 74 or 76), or *Aspergillus fumigatus*, such as one disclosed in SEQ ID NO: 2 in WO 2005/047499 or SEQ ID NO: 8 herein; or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*. In an embodiment the beta-glucosidase is from a strain of *Aspergillus*, such as a strain of *Aspergillus fumigatus*, such as *Aspergillus fumigatus* beta-glucosidase (SEQ ID NO: 8 herein), or a variant thereof, which variant comprises one or more substitutions selected from the group consisting of L89M, G91L, F100D, I140V, I186V, S283G, N456E, and F512Y; such as a variant thereof with the following substitutions:

F100D+S283G+N456E+F512Y;
L89M+G91L+I186V+I140V;
I186V+L89M+G91L+I140V+F100D+S283G+N456E+F512Y.

In an embodiment the parent beta-glucosidase has at least 60% identity, such as at least 70%, such as at least 80%, such as at least 90%, such as at least 95%, such as at least 96%, such as at least 97%, such as at least 98%, such as at least 99% identity to the mature polypeptide of SEQ ID NO: 8 herein.

In case the beta-glucosidase is a beta-glucosidase variant it has at least 60% identity, such as at least 70%, such as at least 80%, such as at least 90%, such as at least 95%, such as at least 96%, such as at least 97%, such as at least 98%, such as at least 99%, but less than 100% identity to the mature polypeptide of SEQ ID NO: 8 herein.

In case the cellulolytic enzyme composition comprises a GH61 polypeptide, it may be one derived from the genus *Thermoascus*, such as a strain of *Thermoascus aurantiacus*, such as the one described in WO 2005/074656 as SEQ ID NO: 2 or SEQ ID NO: 9 herein; or one derived from the genus *Thielavia*, such as a strain of *Thielavia terrestris*, such as the one described in WO 2005/074647 as SEQ ID NO: 7 and SEQ ID NO: 8 (hereby incorporated by reference); or one derived from a strain of *Aspergillus*, such as a strain of *Aspergillus fumigatus*, such as the one described in WO 2010/138754 as SEQ ID NO: 1 and SEQ ID NO: 2 (hereby incorporated by reference); or one derived from a strain from *Penicillium*, such as a strain of *Penicillium emersonii*, such as the one disclosed in WO 2011/041397 as SEQ ID NO: 2 or SEQ ID NO: 10 herein.

In a preferred embodiment the GH61 polypeptide, such as one derived from a strain of *Thermoascus*, is selected from the group consisting of:
(i) a GH61 polypeptide comprising the mature polypeptide of SEQ ID NO: 9 herein;
(ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 9 herein.

In a preferred embodiment the GH61 polypeptide, such as one derived from a strain of *Penicillium* sp., is selected from the group consisting of:
(i) a GH61 polypeptide comprising the mature polypeptide of SEQ ID NO: 10 herein;
(ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 10 herein.

In an embodiment the cellulolytic enzyme composition comprises a cellobiohydrolase I (CBH I), such as one derived from a strain of the genus *Aspergillus*, such as a strain of *Aspergillus fumigatus*, such as the Cel7a CBHI disclosed in SEQ ID NO: 6 in WO 2011/057140 or SEQ ID NO: 6 herein, or a strain of the genus *Trichoderma*, such as a strain of *Trichoderma reesei*.

In a preferred embodiment the cellobiohydrolase I, such as one derived from a strain of *Aspergillus fumigatus*, is selected from the group consisting of:
(i) a cellobiohydrolase I comprising the mature polypeptide of SEQ ID NO: 6 herein;
(ii) a cellobiohydrolase I comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 6 herein.

In an embodiment the cellulolytic enzyme composition, comprised in an enzyme composition of the invention, comprises a cellobiohydrolase II (CBH II), such as one derived from a strain of the genus *Aspergillus*, such as a strain of *Aspergillus fumigatus*; such as the one disclosed as SEQ ID NO: 7 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In a preferred embodiment cellobiohydrolase II, such as one derived from a strain of *Aspergillus fumigatus*, is selected from the group consisting of:
(i) a cellobiohydrolase II comprising the mature polypeptide of SEQ ID NO: 7 herein;
(ii) a cellobiohydrolase II comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 7 herein.

In an embodiment the cellulolytic enzyme composition comprises a GH61 polypeptide having cellulolytic enhancing activity and a beta-glucosidase.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 10 herein, and a beta-glucosidase.

In an embodiment the cellulolytic enzyme composition comprises a GH61 polypeptide having cellulolytic enhancing activity, a beta-glucosidase, and a CBHI.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 10 herein, a beta-glucosidase, and a CBHII.

In an embodiment the cellulolytic enzyme composition, comprised in an enzyme composition of the invention, comprises a GH61 polypeptide having cellulolytic enhancing activity, a beta-glucosidase, a CBHI, and a CBHII.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 10 herein, a beta-glucosidase, a CBHI, and a CBHII.

In an embodiment the cellulolytic enzyme composition is a *Trichoderma reesei* cellulolytic composition further comprising *Thermoascus aurantiacus* GH61A polypeptide (SEQ ID NO: 2 in WO 2005/074656 or SEQ ID NO: 9 herein), and *Aspergillus oryzae* beta-glucosidase fusion protein (WO 2008/057637).

In an embodiment the cellulolytic enzyme composition is a *Trichoderma reesei* cellulolytic composition further comprising *Thermoascus aurantiacus* GH61A polypeptide having cellulolytic enhancing activity (SEQ ID NO: 2 in WO 2005/074656 or SEQ ID NO: 9 herein) and *Aspergillus fumigatus* beta-glucosidase (SEQ ID NO: 2 of WO 2005/047499 or SEQ ID NO: 8 herein).

In an embodiment the cellulolytic enzyme composition is a *Trichoderma reesei* cellulolytic composition further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a variant thereof, which variant has one of, preferably all of, the following substitutions: F100D, S283G, N456E, F512Y, and optionally *Aspergillus fumigatus* CBH1, e.g., the one disclosed as SEQ ID NO: 6 in WO2011/057140 and SEQ ID NO: 6 herein and *Aspergillus fumigatus* CBH II, e.g., the one disclosed as SEQ ID NO: 18 in WO 2011/057140 and as SEQ ID NO: 7 herein.

In an embodiment the cellulolytic enzyme composition comprises one or more of the following components
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof.

In an embodiment the *Aspergillus fumigatus* beta-glucosidase (SEQ ID NO: 8 herein), comprises one or more substitutions selected from the group consisting of L89M, G91L, F100D, I140V, I186V, S283G, N456E, and F512Y; such as a variant thereof, with the following substitutions:
F100D+S283G+N456E+F512Y;
L89M+G91L+I186V+I140V; or
I186V+L89M+G91L+I140V+F100D+S283G+N456E+F512Y (using SEQ ID NO: 8 for numbering).

In an embodiment the cellulolytic composition further comprises the *Penicillium* sp. GH61 polypeptide shown in SEQ ID NO: 10 herein; or a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 10 herein.

Pullulanase

The enzymes present and/or added to saccharification and/or fermentation may optionally further include a pullulanase. The pullulanase may be of any origin, such as fungal or bacterial origin.

In an embodiment the pullulanase is derived from a strain of *Bacillus* sp. such as the one shown in SEQ ID NO: 15 herein or a strain of *Bacillus deramificans*.

In an embodiment the pullulanase, such as one derived from *Bacillus* sp, is selected from the group consisting of:
(i) a pullulanase comprising the mature polypeptide of SEQ ID NO: 15 herein;
(ii) a pullulanase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

Trehalase

According to the invention the enzymes present and/or added to saccharification and/or fermentation may optionally further include a trehalase.

The trehalase may be of any origin, such as fungal or bacterial origin.

In an embodiment the trehalase is of fungal origin, such as derived from a strain of *Trichoderma*, such as *Trichoderma reesei*, such as the one shown in SEQ ID NO: 14 herein.

In an embodiment the trehalase, such as one derived from *Trichoderma reesei*, is selected from the group consisting of:
(i) a trehalase comprising the mature polypeptide of SEQ ID NO: 14 herein;
(ii) a trehalase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 14 herein.

Pectinase

According to the invention the enzymes present and/or added to saccharification and/or fermentation may optionally further include a pectinase, such as a pectin lyase (also known as pectolyase) and/or a polygalacturonase, or a combination thereof.

The pectinase may be of any origin, such as fungal or bacterial origin.

In a preferred embodiment the pectinase is a pectin lyase (EC 4.2.2.10).

In an embodiment the pectin lyase is derived from a strain of *Aspergillus*, such as *Aspergillus niger*.

In a preferred embodiment the pectinase is a polygalacturonase (EC. 3.2.1.15).

In an embodiment the polygalacturonase is derived from a strain of *Aspergillus*, such as *Aspergillus aculeatus*.

In an embodiment the pectinase is a combination of pectin lyase and polygalacturonase. In an embodiment the pectinase is a combination of pectin lyase derived from *Aspergillus niger* and polygalacturonase derived from *Aspergillus aculeatus*.

Examples of Enzymes (e.g., Blend) Suitable for Use in a Raw Starch Hydrolysis Process of the Invention In an embodiment enzymes (e.g., blend) for use in a process of the invention comprise a glucoamylase and an alpha-amylase, and optionally a protease and/or cellulolytic enzyme composition. Other optional enzymes may also be used.

In a preferred embodiment the enzymes (e.g., blend) used in a process of the invention comprises or consists of a glucoamylase from *Trametes cingulata* (e.g., SEQ ID NO: 12) and an alpha-amylase from *Rhizomucor pusillus* with an *Aspergillus niger* glucoamylase linker and starch-binding domain (SBD), e.g., SEQ ID NO: 13.

In a preferred embodiment the enzymes (e.g., blend) used in a process of the invention comprises the *Gloeophyllum trabeum* glucoamylase (e.g., SEQ ID NO: 18 herein) having one or more of the following substitutions: S95P, A121P, preferably S95P+A121P and an alpha-amylase, preferably an alpha-amylase derived from *Rhizomucor pusillus* with an *Aspergillus niger* glucoamylase linker and starch-binding domain (SBD), shown in SEQ ID NO: 13 herein, preferably having one or more of the following substitutions: G128D, D143N, preferably G128D+D143N.

In another preferred embodiment the enzymes (e.g., blend) used in a process of the invention comprises the *Pycnoporus sanguineus* glucoamylase shown in SEQ ID NO: 17 herein and an alpha-amylase, preferably one derived from *Rhizomucor pusillus* with a linker and starch-binding domain (SBD), preferably *Rhizomucor pusillus* with an *Aspergillus niger* glucoamylase linker and starch-binding domain (SBD), in particular the one shown in SEQ ID NO: 13 herein, preferably having one or more of the following substitutions: G128D, D143N, especially G128D+D143N.

In a preferred embodiment the enzymes (e.g., blend) used in a process of the invention comprises the *Gloeophyllum sepiarium* glucoamylase shown in SEQ ID NO: 4 herein and an alpha-amylase, preferably an alpha-amylase derived from *Rhizomucor pusillus* with a linker and starch-binding domain (SBD), preferably *Rhizomucor pusillus* alpha-amylase with an *Aspergillus niger* glucoamylase linker and starch-binding domain (SBD) shown in SEQ ID NO: 13 herein, preferably having one or more of the following substitutions: G128D, D143N, preferably G128D+D143N.

In a preferred embodiment the enzymes (e.g., blend) used in a process of the invention comprises the *Trametes cingulata* glucoamylase shown in SEQ ID NO: 12 herein and an alpha-amylase, preferably an alpha-amylase derived from *Rhizomucor pusillus* with an *Aspergillus niger* glucoamylase linker and starch-binding domain (SBD), shown in SEQ ID NO: 13 herein, having one or more of the following substitutions: G128D, D143N, preferably G128D+D143N.

In an embodiment the enzymes (e.g., blend) used in a process of the invention comprises
  i) fungal glucoamylase;
  ii) fungal alpha-amylase;
  iii) cellulolytic enzyme composition derived from a strain of *Trichoderma reesei*, further comprising a GH61 polypeptide, beta-glucosidase, CBH I and CBH II;
  iv) optionally a protease.

In an embodiment the enzymes (blend) used in a process of the invention comprises
  i) *Trametes cingulata* glucoamylase;
  ii) *Rhizomucor pusillus* alpha-amylase, or variant thereof;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
  iv) optionally a protease from *Thermoascus aurantiacus*, or variant thereof.

In an embodiment the enzymes (e.g., blend) used in a process of the invention comprises a
  i) *Trametes cingulata* glucoamylase;
  ii) *Rhizomucor pusillus* alpha-amylase, or variant thereof;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
  iv) optionally a protease from *Pyropoccus furiosus*.

In an embodiment the enzymes (e.g., blend) used in a process of the invention comprises
  i) glucoamylase derived from *Trametes cingulata;*
  ii) alpha-amylase derived from *Rhizomucor pusillus* with an *Aspergillus niger* glucoamylase linker and starch-binding domain (SBD), or a variant thereof;
  iii) cellulolytic enzyme composition derived from a strain of *Trichoderma reesei;*
  iv) optionally a protease from *Thermoascus aurantiacus*, or a variant thereof and/or *Pyrococcus furiosus*.

In an embodiment the enzymes (e.g., blend) used in a process of the invention comprises
  i) fungal glucoamylase;
  ii) fungal alpha-amylase;
  iii) cellulolytic enzyme composition derived from a strain of *Trichoderma reesei*, further comprising a GH61 polypeptide, beta-glucosidase CBH I and CBH II;
  iv) pectinase, preferably a pectin lyase or a polygalacturonase, or a combination thereof.

In an embodiment the pectinase is a combination of pectin lyase derived from *Aspergillus niger* and polygalacturonase derived from *Aspergillus aculeatus*.

In an embodiment the pectinase is a combination of pectin lyase and polygalacturonase. In an embodiment the pectinase is a combination of pectin lyase derived from *Aspergillus niger* and polygalacturonase derived from *Aspergillus aculeatus*.

In an embodiment the enzymes (e.g., blend) used in a process of the invention comprises
  i) fungal glucoamylase;
  ii) fungal alpha-amylase;
  iii) pectinase, preferably a pectin lyase or a polygalacturonase, or a combination thereof;
  iv) cellulolytic enzyme composition derived from a strain of *Trichoderma reesei*, further comprising a GH61 polypeptide, beta-glucosidase CBH I and CBH II;
  v) protease.

In an embodiment the enzymes (e.g., blend) used in a process of the invention comprises a
  i) fungal glucoamylase;
  ii) fungal alpha-amylase;
  iii) cellulolytic enzyme composition derived from a strain of *Trichoderma reesei*, further comprising a GH61 polypeptide, beta-glucosidase, CBH I and CBH II;
  iv) optionally a protease.

In an embodiment the enzymes (e.g., blend) used in a process of the invention comprises
  i) *Trametes cingulata* glucoamylase;
  ii) *Rhizomucor pusillus* alpha-amylase, or variant thereof;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
  iv) pectin lyase derived from *Aspergillus niger* or polygalacturonase derived from *Aspergillus aculeatus*, or a combination thereof;
  v) protease from *Thermoascus aurantiacus*, or a variant thereof and/or *Pyrococcus furiosus*.

In a preferred embodiment the enzymes (blend) used in a process of the invention comprises
  i) *Gloeophyllum trabeum* glucoamylase shown in SEQ ID NO: 18 herein having one or more of the following substitutions: S95P, A121P, such as S95P+A121P;
  ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
  optionally iv) protease from *Thermoascus aurantiacus*, or a variant thereof.

In a preferred embodiment the enzymes (e.g., blend) used in a process of the invention comprises
  i) *Pycnoporus sanguineus* glucoamylase shown in SEQ ID NO: 17 herein;
  ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;

optionally iv) protease from *Thermoascus aurantiacus*, or a variant thereof.

In a preferred embodiment the enzymes (e.g., blend) used in a process of the invention comprises
  i) *Gloeophyllum sepiarium* glucoamylase shown in SEQ ID NO: 4 herein;
  ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
optionally iv) protease from *Thermoascus aurantiacus*, or a variant thereof.

In a preferred embodiment the enzymes (e.g., blend) used in a process of the invention comprises
  i) *Trametes cingulata* glucoamylase shown in SEQ ID NO: 12 herein;
  ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;
  iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
optionally iv) protease from *Thermoascus aurantiacus*, or a variant thereof.

Examples of Processes of the Invention

A process of the invention of producing ethanol from starch-containing material comprises:
  (i) saccharifying starch-containing material at a temperature below the initial gelatinization temperature; and
  (ii) fermenting using a fermentation organism;
  wherein
    saccharification and/or fermentation is done in the presence of the following enzymes: glucoamylase and alpha-amylase, and optionally protease; and
    the fermenting organism is a *Saccharomyces* yeast strain providing:
      an ethanol yield boost compared to ETHANOL RED™;
      lower glycerol production compared to ETHANOL RED™;
    under the same fermentation conditions.

A process of the invention of producing ethanol from starch-containing material comprises:
  (i) saccharifying starch-containing material at a temperature below the initial gelatinization temperature; and
  (ii) fermenting using a fermentation organism;
  wherein
    saccharification and/or fermentation is done in the presence of the following enzymes: glucoamylase and alpha-amylase, and optionally protease; and the fermenting organism is a *Saccharomyces* yeast strain which:
      provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™; and/or
      provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™.

A process of the invention of producing ethanol from starch-containing material comprises:
  (i) saccharifying starch-containing material at a temperature below the initial gelatinization temperature; and
  (ii) fermenting using a fermentation organism;
  wherein
    saccharification and/or fermentation is done in the presence of the following enzymes: glucoamylase and alpha-amylase, and optionally protease; and
    the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); or
    the fermenting organism is selected from the group of derivatives of *Saccharomyces cerevisiae* MBG 4911, MBG4913 or MBG4914 having the defining characteristics of one or more of these *Saccharomyces cerevisiae* strains.

In a preferred embodiment the process of producing ethanol from starch-containing material of the invention comprises:
(a) saccharifying a starch-containing material at a temperature below the initial gelatinization temperature; and
(b) fermenting using a fermentation organism;
wherein
  saccharification and/or fermentation is done in the presence of the following enzymes:
    i) glucoamylase derived from *Trametes cingulata*, *Gloeophyllum trabeum*, *Gloeophyllum sepiarium*, or *Pycnoporus sanguineus*;
    ii) alpha-amylase derived from *Rhizomucor pusillus* with an *Aspergillus niger* glucoamylase linker and starch-binding domain (SBD), or a variant thereof;
    iii) cellulolytic enzyme composition derived from *Trichoderma reesei*;
    iv) optionally a protease from *Thermoascus aurantiacus*, or a variant thereof and/or *Pyrococcus furiosus*; and
wherein
  the fermenting organism is a *Saccharomyces* yeast strain providing:
    an ethanol yield boost compared to ETHANOL RED™;
    lower glycerol production compared to ETHANOL RED™;
under the same fermentation conditions; preferably
  provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™; and/or provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™; and/or the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); or the fermenting organism is selected from the group of derivatives of *Saccharomyces cerevisiae* MBG 4911, MBG4913 or MBG4914 having the defining characteristics of one or more of these *Saccharomyces cerevisiae* strains.

In a preferred embodiment the process of producing ethanol from starch-containing material of the invention comprises:
(a) saccharifying a starch-containing material at a temperature below the initial gelatinization temperature; and
(b) fermenting using a fermentation organism;
wherein
saccharification and/or fermentation is done in the presence of the following enzymes:
 i) glucoamylase derived from *Gloeophyllum trabeum* disclosed in SEQ ID NO: 18, with the following substitutions: S95P+A121P;
 ii) alpha-amylase derived from *Rhizomucor pusillus* with an *Aspergillus niger* glucoamylase linker and starch-binding domain (SBD), or a variant thereof, shown in SEQ ID NO: 13 herein, with the following substitutions: G128D+D143N;
 iii) cellulolytic enzyme composition derived from *Trichoderma reesei;*
 iv) optionally a protease from *Thermoascus aurantiacus*, or a variant thereof; and
wherein
the fermenting organism is a *Saccharomyces* yeast strain providing:
an ethanol yield boost compared to ETHANOL RED™;
lower glycerol production compared to ETHANOL RED™;
under the same fermentation conditions; preferably
provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™; and/or
provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™; and/or the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); or the fermenting organism is selected from the group of derivatives of *Saccharomyces cerevisiae* MBG 4911, MBG4913 or MBG4914 having the defining characteristics of one or more of these *Saccharomyces cerevisiae* strains.

In a preferred embodiment the process of producing ethanol from starch containing material of the invention comprises:
(a) saccharifying a starch-containing material at a temperature below the initial gelatinization temperature; and
(b) fermenting using a fermentation organism;
wherein
saccharification and/or fermentation is done in the presence of the following enzymes:
 i) glucoamylase derived from *Pycnoporus sanguineus* shown in SEQ ID NO: 17;
 ii) alpha-amylase derived from *Rhizomucor pusillus* with an *Aspergillus niger* glucoamylase linker and starch-binding domain (SBD), or a variant thereof, shown in SEQ ID NO: 13 herein, with the following substitutions: G128D+D143N;
 iii) cellulolytic enzyme composition derived from *Trichoderma reesei;*
 iv) optionally a protease from *Thermoascus aurantiacus*, or a variant thereof; and
wherein
the fermenting organism is a *Saccharomyces* yeast strain providing:
an ethanol yield boost compared to ETHANOL RED™;
lower glycerol production compared to ETHANOL RED™;
under the same fermentation conditions; preferably
provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™; and/or
provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™; and/or the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharo-

*myces cerevisiae* MBG4914 (deposited as V15/001461 at National Measurement Institute, Victoria, Australia); or the fermenting organism is selected from the group of derivatives of *Saccharomyces cerevisiae* MBG 4911, MBG4913 or MBG4914 having the defining characteristics of one or more of these *Saccharomyces cerevisiae* strains.

In a preferred embodiment the process of producing ethanol from starch-containing material of the invention comprises:
(a) saccharifying a starch-containing material at a temperature below the initial gelatinization temperature; and
(b) fermenting using a fermentation organism;
wherein
saccharification and/or fermentation is done in the presence of the following enzymes:
   i) glucoamylase derived from *Gloeophyllum sepiarium* shown in SEQ ID NO: 4;
   ii) alpha-amylase derived from *Rhizomucor pusillus* with an *Aspergillus niger* glucoamylase linker and starch-binding domain (SBD), or a variant thereof, shown in SEQ ID NO: 13 herein, with the following substitutions: G128D+D143N;
   iii) cellulolytic enzyme composition derived from *Trichoderma reesei*;
   iv) optionally a protease from *Thermoascus aurantiacus*, or a variant thereof;
wherein
the fermenting organism is a *Saccharomyces* yeast strain providing:
   an ethanol yield boost compared to ETHANOL RED™;
   lower glycerol production compared to ETHANOL RED™;
under the same fermentation conditions; preferably
   provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™; and/or
   provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™; and/or
   the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); or
   the fermenting organism is selected from the group of derivatives of *Saccharomyces cerevisiae* MBG 4911, MBG4913 or MBG4914 having the defining characteristics of one or more of these *Saccharomyces cerevisiae* strains.

In a preferred embodiment the process of producing ethanol from starch-containing material of the invention comprises:
(a) saccharifying a starch-containing material at a temperature below the initial gelatinization temperature; and
(b) fermenting using a fermentation organism;
wherein
saccharification and/or fermentation is done in the presence of the following enzymes:
   i) glucoamylase derived from *Trametes cingulata* shown in SEQ ID NO: 12;
   ii) alpha-amylase derived from *Rhizomucor pusillus* with an *Aspergillus niger* glucoamylase linker and starch-binding domain (SBD), or a variant thereof, shown in SEQ ID NO: 13 herein, with the following substitutions: G128D+D143N;
   iii) cellulolytic enzyme composition derived from *Trichoderma reesei*;
   iv) optionally a protease from *Thermoascus aurantiacus*, or a variant thereof; and
wherein
the fermenting organism is a *Saccharomyces* yeast strain providing:
   an ethanol yield boost compared to ETHANOL RED™;
   lower glycerol production compared to ETHANOL RED™;
under the same fermentation conditions; preferably
   provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™; and/or
   provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™; and/or
   the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); or
   the fermenting organism is selected from the group of derivatives of *Saccharomyces cerevisiae* MBG 4911, MBG4913 or MBG4914, respectively, having the defining characteristics of one or more of these *Saccharomyces cerevisiae* strains.

Yeast of the Invention

In this aspect the invention relates to *Saccharomyces* yeast strains with improved properties in ethanol production processes.

The majority of the world's fuel ethanol is produced by industrial scale fermentation of starch-based sugars, in substrates such as corn mash. During industrial scale fermentation, the yeast encounter various physiological challenges including variable concentrations of sugars, high concentrations of yeast metabolites such as ethanol, glycerol, organic acids, osmotic stress, as well as potential competition from contaminating microbes such as wild yeasts and bacteria. As a consequence, many *Saccharomyces* strains are not suitable for use in industrial fermentation. The most widely used commercially available industrial strain of *Saccharomyces* (i.e. for industrial scale ethanol fermentation) is the *Saccharomyces cerevisiae* strain, e.g., sold under the trade name ETHANOL RED™.

The inventors have now provided *Saccharomyces* yeast strains providing higher ethanol yield compared to ETHANOL RED™
lower glycerol production compared to ETHANOL RED™;

under the same fermentation conditions.

The strains of the invention are non-recombinant *Saccharomyces* strains. The strains of the invention may be produced using the methods described in WO 2005/121337 and through matings with various strains of *Saccharomyces cerevisiae* combined with selection for characteristics including low glycerol production and high ethanol production in a raw starch ethanol production process. This is described further in Example 1 below.

As used herein, a defining characteristic of a non-recombinant *Saccharomyces cerevisiae* strain of the invention is any one or more of the following characteristics:

i) provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™.

ii) provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™.

Specific embodiments of yeast strains of the invention can be selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia).

A yeast strain of the invention may also be a derivative of *Saccharomyces cerevisiae MBG*4911, MBG4913 or MBG4914, respectively, having the defining characteristics of one or more of these *Saccharomyces cerevisiae* strains.

In an embodiment yeast strains of the invention grow on xylose as a sole carbon source, e.g., determined using the Test T1 described below in the "Materials & Methods" section. As current wild type and industrial strains of *Saccharomyces* are not capable of growth on xylose at the rate at which strains of the invention, in particular *Saccharomyces* MBG4911, MBG4913 and MBG4914, respectively, grow on xylose, the strains of the invention are readily differentiated from current wild type strains of *Saccharomyces* yeast and strains of *Saccharomyces* yeast that are used in the ethanol industry prior to the present invention such as ETHANOL RED™.

Further, in an embodiment a *Saccharomyces* yeast strain of the invention shows more than two-fold increase in biomass, such as more than six-fold increase in biomass, such as more than 20-fold increase in biomass determined using the Test T1 described in the "Materials & Methods" section.

According to the invention the yeast of the invention may be in any viable form, including crumbled, dry, including active dry and instant, compressed, cream form etc. In a preferred embodiment the *Saccharomyces cerevisiae* yeast strain used in a process of the invention is dry yeast, such as active dry yeast. In a preferred embodiment the *Saccharomyces cerevisiae* yeast strain used in a process of the invention is compressed yeast. In an embodiment the *Saccharomyces cerevisiae* yeast strain used in a process of the invention is cream yeast. In an embodiment a *Saccharomyces cerevisiae* strain of the invention is dry yeast.

The invention also relates to a derivative of *Saccharomyces* strain of the invention including *Saccharomyces* MBG4911, MBG4913 and MBG4914.

As used herein, a "derivative" is a yeast strain derived from a yeast strain of the invention (e.g., *Saccharomyces* MBG4911, MBG4913 and MBG4914), including through mutagenesis, recombinant DNA technology, mating, cell fusion, or cytoduction between yeast strains. The strain may be a direct progeny (i.e. the product of a mating between a strain of the invention and another strain or itself), or a distant progeny resulting from an initial mating between a strain of the invention and another strain or itself, followed by a large number of subsequent matings.

In one embodiment, a derivative strain is a hybrid strain produced by culturing a first yeast strain with a strain of the invention, in particular *Saccharomyces* MBG4911, MBG4913 and MBG4914, under conditions which permit combining of DNA between the first yeast strain and a strain of the invention.

In an embodiment the invention relates to methods of producing a derivative of a yeast strain of the invention, in particular a derivative of *Saccharomyces* MBG 4911, MBG4913 or MBG4914, respectively, which exhibits the defining characteristics of a strain of the invention, in particular *Saccharomyces* MBG 4911, MBG4913 or MBG4914, respectively, comprising:

(a) providing:
(i) a first yeast strain; and
(ii) a second yeast strain, wherein the second yeast strain is a yeast strain of the invention, in particular strain *Saccharomyces* MBG4911, MBG4913 or MBG4914, respectively, or a derivative of yeast strain of the invention, in particular a derivative of *Saccharomyces* MBG 4911, MBG4913 or MBG4914, respectively;
(b) culturing the first yeast strain and the second yeast strain under conditions which permit combining of DNA between the first and second yeast strains;
(c) screening or selecting for a derivative strain.

In an embodiment step (c) comprises screening or selecting for a hybrid strain which exhibits one or more defining characteristic of strain *Saccharomyces* MBG4911, MBG4913 or MBG4914, respectively.

In an embodiment method comprises the further step of:
(d) repeating steps (b) and (c) with the screened or selected strain from step (c) as the first and/or second yeast strain, until a derivative is obtained which exhibits the defining characteristics of a yeast strain of the invention, in particular *Saccharomyces* MBG4911, MBG4913, or MBG4914, respectively.

In an embodiment the culturing step (b) comprises:
(i) sporulating the first yeast strain and the second yeast strain;

(ii) hybridizing germinated spores produced by the first yeast strain with germinated spores produced by the second yeast strain.

In an embodiment the derivative of a *Saccharomyces* yeast strain of the invention is produced by the method described above. The method comprises incubating a yeast strain of the invention, in particular *Saccharomyces* MBG4911, MBG4913, or MBG4914, respectively, with a substrate comprising a fermentable sugar under conditions which permit fermentation of the fermentable sugar to produce ethanol.

In an embodiment the invention relates to use of a strain of the invention, in particular *Saccharomyces* MBG4911, MBG4913, or MBG4914, respectively, in a process of producing ethanol of the invention.

In an embodiment the invention relates to the use of a strain of the invention, in particular *Saccharomyces cerevisiae* MBG4911, MBG4913 or MBG4914, respectively, or a derivative thereof in a process of the invention.

In one embodiment, a derivative of a yeast strain of the invention, in particular *Saccharomyces* MBG4911, MBG4913 and MBG4914, is a hybrid strain produced by culturing a first strain with a strain of the invention, in particular *Saccharomyces* MBG4911, MBG4913 and MBG4914, under conditions which permit combining of DNA between the first yeast strain and a strain of the invention, in particular MBG4911, MBG4913 and MBG4914, respectively.

In one embodiment, a derivative yeast strain of the invention may be prepared by:
 (a) culturing a first yeast strain with a second yeast strain, wherein the second yeast strain is a yeast strain of the invention, in particular *Saccharomyces* MBG4911, MBG4913 or MBG4914, respectively, or a derivative of a strain of the invention, under conditions which permit combining of DNA between the first yeast strain and the second yeast strain; and
 (b) isolating hybrid strains; and
 (c) optionally repeating steps (a) and (b) using a hybrid strain isolated in step (b) as the first yeast strain and/or the derivative of a strain of the invention.

In one embodiment, the derivative of a strain of the invention exhibits one or more defining characteristic of a yeast strain of the invention, in particular *Saccharomyces* MBG4911, MBG4913 or MBG4914, respectively. Derivatives of *Saccharomyces* yeast which exhibit one or more defining characteristics are produced using a yeast strain of the invention. In this regard, a yeast strain of the invention, in particular *Saccharomyces* MBG4911, MBG4913 or MBG4914, respectively, forms the basis for preparing other yeast strains having the defining characteristics of a yeast strain of the invention, in particular *Saccharomyces* MBG4911, MBG4913, or MBG4914, respectively. For example, strains of *Saccharomyces* yeast which exhibit one or more defining characteristics of a yeast strain of the invention can be derived from a yeast strain of the invention using methods such as classical mating, cell fusion, or cytoduction between yeast strains, mutagenesis or recombinant DNA technology.

In one embodiment, a derivative of a yeast strain of the invention which exhibits one or more defining characteristics of a strain of the invention, in particular *Saccharomyces* MBG4911, MBG4913 and MBG4914, respectively, may be produced by:
 (a) culturing a first yeast strain with a second yeast strain, wherein the second yeast strain is a strain of the invention, in particular *Saccharomyces* MBG4911, MBG4913 or MBG4914, respectively, or a derivative thereof, under conditions which permit combining of DNA between the first yeast strain and the second yeast strain;
 (b) screening or selecting for a derivative strain, such as screening or selecting for a derivative with higher ethanol yield, e.g., in corn mash, compared to the first strain, and/or screening or selecting for a hybrid which has a lower glycerol production, e.g., in corn mash, compared to the first strain;
 (c) optionally repeating steps (a) and (b) with the screened or selected strain as the first yeast strain and/or the second yeast strain, until a derivative strain is obtained which exhibits one or more defining characteristics of a strain of the invention, in particular *Saccharomyces* MBG4911, MBG4913 and MBG4914, respectively.

The first yeast strain may be any strain of yeast if the DNA of the strain can be combined with the second yeast strain using methods such as classical mating, cell fusion or cytoduction. Typically, the first yeast strain is a *Saccharomyces* yeast strain. More typically, the first yeast strain is a *Saccharomyces cerevisiae* yeast strain. *Saccharomyces cerevisiae* is as defined by Kurtzman (2003) FEMS Yeast Research vol 4 pp. 233-245. The first yeast strain may have desired properties which are sought to be combined with the defining characteristics of a strain of the invention, in particular MBG4911, MBG4913 and MBG4914, respectively. The first yeast strain may be, for example, any *Saccharomyces cerevisiae* strain, such as for example ETHANOL RED™. It will also be appreciated that the first yeast strain may be a strain of the invention or a strain which exhibits one or more defining characteristics of a strain of the invention.

The first and second yeast strains are cultured under conditions which permit combining of DNA between the yeast strains. As used herein, "combining of DNA" between yeast strains refers to combining of all or a part of the genome of the yeast strains. Combining of DNA between yeast strains may be by any method suitable for combining DNA of at least two yeast cells, and may include, for example, mating methods which comprise sporulation of the yeast strains to produce haploid cells and subsequent hybridising of compatible haploid cells; cytoduction; or cell fusion such as protoplast fusion.

In one embodiment, culturing the first yeast strain with the second yeast strain, under conditions which permit combining of DNA between the first yeast strain and the second yeast strain, comprises:
 (i) sporulating the first yeast strain and the second yeast strain;
 (ii) germinating and hybridizing spores produced by the first yeast strain with spores produced by the second yeast strain.

In one embodiment, the method of producing a derivative of a yeast strain of the invention, in particular *Saccharomyces* MBG4911, MBG4913, or MBG4914, respectively, which exhibits one or more defining characteristics of a yeast strain of the invention, comprises:
 (a) providing: (i) a first yeast strain; and (ii) a second yeast strain, wherein the second yeast strain is a strain of the invention, in particular *Saccharomyces* MBG4911, MBG4913, or MBG4914, respectively, or a derivative thereof;
 (b) sporulating the first yeast strain and the second yeast strain;

(c) germinating and hybridising the spores of the first yeast strain with germinated spores of the second yeast strain;

(d) screening or selecting for a derivative of a strain of the invention, such as screening or selecting for a derivative with higher ethanol yield, e.g., in corn mash, compared to the first strain, and/or screening or selecting for a hybrid with lower glycerol production, e.g., in corn mash, compared to the first strain;

(e) optionally repeating steps (b) to (d) with the screened or selected strain as the first and/or second yeast strain.

Methods for sporulating, germinating and hybridising yeast strains, and in particular, Saccharomyces strains, are known in the art and are described in, for example, Ausubel, F. M. et al., (1997) Current Protocols in Molecular Biology, Volume 2, pages 13.2.1 to 13.2.5 (John Willey & Sons Inc); Chapter 7, "Sporulation and Hybridisation of yeast" by R. R. Fowell, in "The Yeasts" vol 1, A. H. Rose and J. S. Harrison (Eds), 1969, Academic Press.

In one embodiment, the yeast strains may be cultured under conditions which permit cell fusion. Methods for the generation of intraspecific or interspecific hybrids using cell fusion techniques are described in, for example, Spencer et al. (1990) in, Yeast Technology, Spencer J F T and Spencer D M (Eds), Springer Verlag, New York.

In another embodiment, the yeast strains may be cultured under conditions which permit cytoduction. Methods for cytoduction are described in, for example, Inge-Vechymov et al. (1986) Genetika 22: 2625-2636; Johnston (1990) in, Yeast technology, Spencer J F T and Spencer D M (Eds), Springer Verlag, New York.

In one embodiment, screening or selecting for derivatives of a strain of the invention, in particular Saccharomyces MBG4911, MBG4913, or MBG4914, respectively, comprises screening or selecting for a derivative with higher ethanol production, e.g., in corn mash, compared to the first strain, and/or screening or selecting for a hybrid which produces less glycerol, e.g., in corn mash, compared to the first strain.

Methods for determining the amount of ethanol and glycerol produced by a strain are known in the art. For example, methods for testing for determining the amount of ethanol and glycerol produced by a strain during fermentation of corn mash are described in, for example, WO 2011/035392.

Once the amount of ethanol and glycerol produced are known, the ratio of ethanol/glycerol can be readily determined. Accordingly, strains can be readily screened for production levels of ethanol and/or glycerol using known methods.

In one embodiment, a derivative of a strain of the invention, in particular Saccharomyces MBG4911, MBG4913, or MBG4914, respectively, which exhibits one or more defining characteristics of a strain of the invention, may be a mutant of a strain. Methods for producing mutants of Saccharomyces yeast, and specifically mutants of Saccharomyces cerevisiae, are known in the art and described in, for example, Lawrence C. W. (1991) Methods in Enzymology, 194: 273-281.

In another embodiment, a derivative of a strain of the invention, in particular Saccharomyces MBG4911, MBG4913, or MBG4914, which exhibits one or more defining characteristics of a strain of the invention, may be a recombinant derivative of a strain of the invention, in particular Saccharomyces MBG4911, MBG4913, or MBG4914.

A recombinant derivative of a strain of the invention, in particular Saccharomyces MBG4911, MBG4913, or MBG4914, respectively, is a strain produced by introducing into a strain of the invention, in particular Saccharomyces MBG4911, MBG4913, or MBG4914, a nucleic acid using recombinant DNA technology. Methods for the introduction of nucleic acid into Saccharomyces yeast cells, and in particular strains of Saccharomyces, are known in the art and are described in, for example, Ausubel, F. M. et al. (1997), Current Protocols in Molecular Biology, Volume 2, pages 13.7.1 to 13.7.7, published by John Wiley & Sons Inc.

Composition of the Invention

In this aspect the invention relates to a formulated Saccharomyces yeast composition comprising a yeast strain of the invention and a naturally occurring and/or a nonenaturally occurring component.

As mentioned above a Saccharomyces yeast strain, in particular Saccharomyces cerevisiae yeast strain, of the invention, may according to the invention may be in any viable form, including crumbled, dry, including active dry and instant, compressed, cream form etc. In a preferred embodiment the Saccharomyces cerevisiae yeast strain of the invention is dry yeast, such as active dry yeast or instant yeast. In a preferred embodiment the Saccharomyces cerevisiae yeast strain of the invention is crumbled yeast In a preferred embodiment the Saccharomyces cerevisiae yeast strain is compressed yeast. In an embodiment the Saccharomyces cerevisiae yeast strain of the invention is cream yeast.

In an embodiment the invention relates to a composition comprising a Saccharomyces yeast of the invention, in particular Saccharomyces MBG4911, MBG4913 or MBG4914, respectively, and one or more of the component selected from the group consisting of: surfactants, emulsifiers, gums, swelling agent, and antioxidants and other processing aids.

Surfactant

According to the invention the composition may comprise a Saccharomyces yeast of the invention, in particular Saccharomyces MBG4911, MBG4913 or MBG4914, respectively, and any suitable surfactant. In an embodiment the surfactant(s) is/are an anionic surfactant, cationic surfactant, and/or nonionic surfactant.

Emulsifier

According to the invention the composition may comprise a Saccharomyces yeast of the invention, in particular Saccharomyces MBG4911, MBG4913 or MBG4914, respectively, and any suitable emulsifier. In an embodiment the emulsifier is a fatty-acid ester of sorbitan. In an embodiment the emulsifier is selected from the group of sorbitan monostearate (SMS), citric acid esters of monodiglycerides, polyglycerolester, fatty acid esters of propylene glycol.

In an embodiment the composition of the invention comprises a Saccharomyces yeast of the invention, in particular Saccharomyces MBG4911, MBG4913 or MBG4914, respectively, and Olindronal SMS, Olindronal SK, or Olindronal SPL including composition concerned in European Patent No. 1,724,336 (hereby incorporated by reference). These products are commercially available from Bussetti, Austria, for active dry yeast.

Gum

According to the invention the composition may comprise a Saccharomyces yeast of the invention, in particular Saccharomyces MBG4911, MBG4913 or MBG4914, respectively, and any suitable gum. In an embodiment the gum is acacia gum, in particular for cream, compressed and dry yeast.

Swelling Agents

According to the invention the composition may comprise a *Saccharomyces* yeast of the invention, in particular *Saccharomyces* MBG4911, MBG4913 or MBG4914, respectively, and any suitable swelling agent. In an embodiment the swelling agent is methyl cellulose or carboxymethyl cellulose.

Antioxidant

According to the invention the composition may comprise a *Saccharomyces* yeast of the invention, in particular *Saccharomyces* MBG4911, MBG4913 or MBG4914, respectively, and any suitable anti-oxidant. In an embodiment the antioxidant is butylated hydroxyanisol (BHA) and/or butylated hydroxytoluene (BHT), or ascorbic acid (vitamin C), particular for active dry yeast.

As used herein, the singular forms "a", "an" and "the" include plural reference unless the context clearly indicates otherwise. Thus, for example, a reference to "a cell" includes a plurality of such cells. Unless defined otherwise, all technical and scientific terms used herein have the same meaning as commonly understood by one of ordinary skill in the art.

As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention may be further described by the following numbered paragraphs:

[1]. A process of producing ethanol from starch-containing material comprising:
   (a) saccharifying starch-containing material at a temperature below the initial gelatinization temperature; and
   (b) fermenting using a fermentation organism;
   wherein
      saccharification and/or fermentation is done in the presence of the following enzymes: glucoamylase and alpha-amylase, and optionally protease; and
      the fermenting organism is a *Saccharomyces* yeast strain providing:
         an ethanol yield boost compared to ETHANOL RED™;
         lower glycerol production compared to ETHANOL RED™;
   under the same fermentation conditions.

[2]. The process of paragraph [1], wherein the fermenting organism grows on xylose as a sole carbon source, e.g., determined using the Test T1.

[3]. The process of paragraph [2], wherein the fermenting organism shows more than two-fold increase in biomass, such as more than six-fold increase in biomass, such as more than 20-fold increase in biomass determined using the Test T1.

[4]. The process of any of paragraphs [1]-[3], wherein the fermenting organism provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6% after 88 hours, at the conditions defined in Example 3 or Example 4, compared to ETHANOL RED™.

[5]. The process of any of paragraphs [1]-[4], wherein the fermenting organism provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™.

[6]. The process of any of paragraphs [1]-[5], wherein the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia).

[7]. The process of any of paragraphs [1]-[6], wherein the fermenting organism is selected from the group of derivatives of *Saccharomyces cerevisiae* MBG4911, MBG4913 andr MBG4914 having the defining characteristics of one or more of these *Saccharomyces* 30 *cerevisiae* strains.

[8]. The process of any of paragraphs [1]-[7], wherein the *Saccharomyces cerevisiae* yeast strain is in a viable form, such as in particular dry yeast, cream yeast, or compressed yeast

[9]. The process of any of paragraphs [1]-[8], wherein the glucoamylase is a *Gloeophyllum* glucoamylase, preferably *Gloeophyllum trabeum* glucoamylase.

[10]. The process of any of paragraphs [1]-[9], wherein the glucoamylase, e.g., derived from *Gloeophyllum trabeum*, is selected from the group consisting of:
   (i) a glucoamylase comprising the mature polypeptide of SEQ ID NO: 18 herein;
   (ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.

[11]. The process of any of paragraphs [1]-[10], wherein the glucoamylase is the *Gloeophyllum trabeum* glucoamylase shown in SEQ ID NO: 18 having one of the following substitutions: V59A; S95P; A121P; T119W; S95P+A121P; V59A+S95P; S95P+T119W; V59A+S95P+A121P; or S95P+T119W+A121P, especially S95P+A121P.

[12]. The process of any of paragraphs [1]-[11], wherein the glucoamylase is a *Trametes* glucoamylase, preferably *Trametes cingulata* glucoamylase.

[13]. The process of any of paragraphs [1]-[12], wherein the glucoamylase, e.g., derived from *Trametes cingulata*, is selected from the group consisting of:
   (i) a glucoamylase comprising the mature polypeptide of SEQ ID NO: 12 herein;
   (ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 12 herein.

[14]. The process of any of paragraphs [1]-[13], wherein the alpha-amylase is, e.g., derived from *Rhizomucor pusillus*, preferably with an *Aspergillus niger* glucoamylase linker and starch-binding domain (SBD), preferably the one disclosed as V039 in Table 5 in WO 2006/069290 or SEQ ID NO: 13 herein.

[15]. The process of any of paragraphs [1]-[14], wherein the alpha-amylase, e.g., derived from *Rhizomucor pusillus*, is selected from the group consisting of:
(i) an alpha-amylase comprising the mature polypeptide of SEQ ID NO: 13 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 13 herein.

[16]. The process any of paragraphs [1]-[15], wherein the glucoamylase is the *Trametes cingulata* glucoamylase shown in SEQ ID NO: 12 and the alpha-amylase is *Rhizomucor pusillus* alpha-amylase with an *Aspergillus niger* glucoamylase linker and starch-binding domain (SBD).

[17]. The process of any of paragraphs [1]-[16], wherein the alpha-amylase is *Rhizomucor pusillus* alpha-amylase with an *Aspergillus niger* glucoamylase linker and starch-binding domain (SBD), preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering).

[18]. The process any of paragraphs [1]-[17], wherein the glucoamylase is the *Gloeophyllum trabeum* glucoamylase shown in SEQ ID NO: 18 having one of the following substitutions: S95P+A121P and the alpha-amylase is *Rhizomucor pusillus* alpha-amylase with an *Aspergillus niger* glucoamylase linker and starch-binding domain (SBD), preferably one having the following substitutions G128D+D143N (using SEQ ID NO: 13 for numbering).

[19]. The process of any of paragraphs [1]-[18], wherein the glucoamylase is derived from *Pycnoporus*, in particular the *Pycnoporus sanguineus*, preferably the glucoamylase shown in SEQ ID NO: 17 herein.

[20]. The process of any of paragraphs [1]-[19], wherein the glucoamylase, e.g., derived from *Pycnoporus sanguineus*, is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

[21]. The process of any of paragraphs [1]-[20], wherein the glucoamylase is the *Pycnoporus sanguineus* glucoamylase shown in SEQ ID NO: 17 herein and the alpha-amylase is the *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein, preferably one having one or more of the following substitutions: G128D, D143N, especially G128D+D143N.

[22]. The process of any of paragraphs [1]-[21], wherein the ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase:mg EP alpha-amylase).

[23]. The process of any of paragraphs [1]-[22], wherein the total dose of glucoamylase and alpha-amylase added is from 10-1,000 µg/g DS, such as from 50-500 µg/g DS, such as 75-250 µg/g DS.

[24]. The process of any of paragraphs 1-24, wherein the total dose of cellulolytic enzyme composition added is from 10-500 µg/g DS, such as from 20-400 µg/g DS, such as 20-300 µg/g DS.

[25]. The process of any of paragraphs [1]-[24], wherein the dose of protease added is from 1-200 µg/g DS, such as from 2-100 µg/g DS, such as 3-50 µg/g DS.

[26]. The process of any of paragraphs [1]-[21], wherein the fermenting organism is a non-recombinant *Saccharomyces* strain, preferably non-recombinant *Saccharomyces cerevisiae* strain.

[27]. The process of any of paragraphs [1]-[26], wherein the fermenting organism strain is a non-recombinant *Saccharomyces* strain preferably non-recombinant *Saccharomyces cerevisiae* strain produced using the method described and concerned in U.S. Pat. No. 8,257,959-BB.

[28]. The process of any of paragraphs [1]-[27], wherein saccharification and fermentation are done separately or simultaneously.

[29]. The process of any of paragraphs [1]-[28], wherein the ethanol (i.e., product) is recovered after fermentation.

[30]. The process of any of paragraphs [1]-[29], wherein the starch-containing material is plant material selected from the corn (maize), cobs, wheat, barley, rye, milo, sago, cassava, tapioca, sorghum, rice, peas, beans, sweet potatoes, oats, or a mixture thereof, preferably corn.

[31]. The process of any of paragraphs [1]-[30], wherein the starch-containing material is granular starch.

[32]. The process of any of paragraphs [1]-[31], wherein the process is carried out at a pH in the range between 3 and 7, preferably from 3 to 6, or more preferably from 3.5 to 5.0.

[33]. The process of any of paragraphs [1]-[32], wherein the dry solid content (DS) lies in the range from 10-55 wt.-% (DS), preferably 25-45 wt.-%, more preferably 30-40% of starch-containing material.

[34]. The process of any of paragraphs [1]-[33], wherein the sugar concentration is kept at a level below about 6 wt.-%, preferably 3 wt.-%, during saccharification and fermentation, especially below 0.25 wt.-%.

[35]. The process of any of paragraphs [1]-[34], wherein a slurry comprising starch-containing material reduced in particle size and water, is prepared before step (a).

[36]. The process of any of paragraphs [1]-[35], wherein the starch-containing material is prepared by reducing the particle size of the starch-containing material, preferably by milling, such that at least 50% of the starch-containing material has a particle size of 0.1-0.5 mm.

[37]. The process of any of paragraphs [1]-[36], wherein the starch-containing plant material is reduced in particle size, such as by dry or wet milling or using particle size emulsion technology.

[38]. The process of any of paragraphs [1]-[37], wherein the fermentation is carried out for 30 to 150 hours, preferably 48 to 96 hours.

[39]. The process of any of paragraphs [1]-[34], wherein the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

[40]. The process of any of paragraphs [1]-[39], wherein further a protease is present during saccharification and/or fermentation.
[41]. The process of any of paragraphs [1]-[40], wherein the glucoamylase is present and/or added in an amount of 0.001 to 10 AGU/g DS, preferably from 0.01 to 5 AGU/g DS, especially 0.1 to 0.5 AGU/g DS.
[42]. The process of any of paragraphs [1]-[41], wherein the glucoamylase is present and/or added in an amount of 10-1,000 micro grams Enzyme Protein/g DS
[43]. The process of any of paragraphs [1]-[42], wherein the alpha-amylase is present and/or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.
[44]. The process of any of paragraphs [1]-[43], wherein the alpha-amylase is present and/or added in an amount of 10-1,000 micro grams Enzyme Protein/g DS.
[45]. The process of any of paragraphs [1]-[44], wherein a cellulolytic enzyme composition is present and/or added during saccharification, fermentation or simultaneous saccharification and fermentation.
[46]. The process of paragraph [45], wherein the cellulolytic enzyme composition is present and/or added in an amount 1-10,000 micrograms EP/g DS, such as 2-5,000, such as 3 and 1,000, such as 4 and 500 micrograms EP/g DS.
[47]. The process of any of paragraphs [45]-[46], wherein cellulolytic enzyme composition is present and/or added in an amount in the range from 0.1-100 FPU per gram total solids (TS), preferably 0.5-50 FPU per gram TS, especially 1-20 FPU per gram TS.
[48]. The process of any of paragraphs [1]-[47], wherein protease is present and/or added in an amount in the range 1-1,000 μg EP/g DS, such as 2-500 μg EP/g DS, such as 3-250 μg EP/g DS.
[49]. The process of any of paragraphs [1]-[48], wherein the fermenting organism is added to fermentation, so that the count per mL of fermentation medium is in the range from $10^5$ to $10^{12}$, preferably from $10^7$ to $10^{10}$, especially about $5 \times 10^7$.
[50]. The process of any of paragraphs [1]-[49], comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase derived from *Trametes cingulata;*
  ii) alpha-amylase derived from *Rhizomucor pusillus* with an *Aspergillus niger* glucoamylase linker and starch-binding domain (SBD), or a variant thereof;
wherein the fermenting organism is a *Saccharomyces* strain providing:
  an ethanol yield boost compared to ETHANOL RED™;
  lower glycerol production compared to ETHANOL RED™;
under the same fermentation conditions; preferably
  wherein the fermenting organism provides an ethanol yield boost of at least 0.5%, preferably at least 1.0%, more preferably at least 1.2%, even more preferably at least 1.5%, such as between 0.5-5%, e.g., 1.0-3.0%, after 72 hours at the conditions defined in Example 2, compared to ETHANOL RED™; and/or
  wherein the fermenting organism provides a lower glycerol production of at least 5%, preferably at least 10%, more preferably at least 15%, such as between 5-25%, such as 10-20% after 72 hours, at the conditions defined in Example 3, compared to ETHANOL RED™; in particular wherein the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); and/or
  wherein the fermenting organism is selected from the group of derivatives of *Saccharomyces cerevisiae* MBG 4911, MBG4913 or MBG4914 having the defining characteristics of one or more of these *Saccharomyces cerevisiae* strains.
[51]. The process of any of paragraphs [1]-[50], comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase derived from *Trametes cingulata;*
  ii) alpha-amylase derived from *Rhizomucor pusillus* with an *Aspergillus niger* glucoamylase linker and starch-binding domain (SBD), or a variant thereof;
  iii) cellulolytic enzyme composition derived from a strain of *Trichoderma reesei;*
  optionally iv) a protease from *Thermoascus aurantiacus*, or a variant thereof and/or *Pyrococcus furiosus;*
wherein the fermenting organism is a *Saccharomyces* strain providing:
  an ethanol yield boost compared to ETHANOL RED™;
  lower glycerol production compared to ETHANOL RED™;
under the same fermentation conditions; preferably
  wherein the fermenting organism provides an ethanol yield boost of at least 0.5%, preferably at least 1.0%, more preferably at least 1.2%, even more preferably at least 1.5%, such as between 0.5-5%, e.g., 1.0-3.0%, after 72 hours at the conditions defined in Example 2, compared to ETHANOL RED™; and/or
  wherein the fermenting organism provides a lower glycerol production of at least 5%, preferably at least 10%, more preferably at least 15%, such as between 5-25%, such as 10-20% after 72 hours, at the conditions defined in Example 3, compared to ETHANOL RED™;
  in particular wherein the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); and/or
  wherein the fermenting organism is selected from the group of derivatives of *Saccharomyces cerevisiae* MBG 4911, MBG4913 or MBG4914 having the defining characteristics of one or more of these *Saccharomyces cerevisiae* strains.
[52]. The process of any of paragraphs [1]-[51], comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase derived from *Gloeophyllum trabeum* shown in SEQ ID NO: 18, preferably having at least one of the following substitutions: V59A; S95P; A121P; T119W; S95P+A121P; V59A+S95P; S95P+T119W; V59A+S95P+

A121P; or S95P+T119W+A121P, especially S95P+A121P (using SEQ ID NO: 18 for numbering);

ii) alpha-amylase derived from *Rhizomucor pusillus* with an *Aspergillus niger* glucoamylase linker and starch-binding domain (SBD), preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering);

wherein the fermenting organism is a *Saccharomyces* strain providing:

an ethanol yield boost compared to ETHANOL RED™;
lower glycerol production compared to ETHANOL RED™;

under the same fermentation conditions; preferably wherein the fermenting organism provides an ethanol yield boost of at least 0.5%, preferably at least 1.0%, more preferably at least 1.2%, even more preferably at least 1.5%, such as between 0.5-5%, e.g., 1.0-3.0%, after 72 hours at the conditions defined in Example 2, compared to ETHANOL RED™; and/or wherein the fermenting organism provides a lower glycerol production of at least 5%, preferably at least 10%, more preferably at least 15%, such as between 5-25%, such as 10-20% after 72 hours, at the conditions defined in Example 3, compared to ETHANOL RED™; in particular wherein the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); and/or wherein the fermenting organism is selected from the group of derivatives of *Saccharomyces cerevisiae* MBG 4911, MBG4913 or MBG4914 having the defining characteristics of one or more of these *Saccharomyces cerevisiae* strains.

[53]. The process of any of paragraphs [1]-[52], comprising:
(a) saccharifying a starch-containing material at a temperature below the initial gelatinization temperature; and
(b) fermenting using a fermentation organism;
wherein saccharification and/or fermentation is done in the presence of the following enzymes:

i) glucoamylase derived from *Gloeophyllum trabeum* shown in SEQ ID NO: 18, preferably having at least one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 18 for numbering);

ii) alpha-amylase derived from *Rhizomucor pusillus* with an *Aspergillus niger* glucoamylase linker and starch-binding domain (SBD), preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering);

iii) cellulolytic enzyme composition derived from a strain of *Trichoderma reesei*; preferably a cellulolytic enzyme composition derived from *Trichoderma reesei* further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y and optionally *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein;

optionally iv) a protease derived from *Thermoascus aurantiacus*, or a variant thereof, and/or *Pyrococcus furiosus*;

wherein the fermenting organism is a *Saccharomyces* strain providing:

an ethanol yield boost compared to ETHANOL RED™;
lower glycerol production compared to ETHANOL RED™;

under the same fermentation conditions; preferably wherein the fermenting organism provides an ethanol yield boost of at least 0.5%, preferably at least 1.0%, more preferably at least 1.2%, even more preferably at least 1.5%, such as between 0.5-5%, e.g., 1.0-3.0%, after 72 hours at the conditions defined in Example 2, compared to ETHANOL RED™; and/or wherein the fermenting organism provides a lower glycerol production of at least 5%, preferably at least 10%, more preferably at least 15%, such as between 5-25%, such as 10-20% after 72 hours, at the conditions defined in Example 3, compared to ETHANOL RED™;

in particular wherein the fermenting organism is selected from the group consisting of 10 *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); and/or wherein the fermenting organism is selected from the group of derivatives of *Saccharomyces cerevisiae* MBG 4911, MBG4913 or MBG4914 having the defining characteristics of one or more of these *Saccharomyces cerevisiae* strains.

[54]. The process of any of paragraphs [1]-[53], comprising:
(i) saccharifying a starch-containing material at a temperature below the initial gelatinization temperature; and
(ii) fermenting using a fermentation organism;
wherein saccharification and/or fermentation is done in the presence of the following enzymes:

i) glucoamylase derived from *Pycnoporus sanguineus* shown in SEQ ID NO: 17 herein,
ii) alpha-amylase derived from *Rhizomucor pusillus* with an *Aspergillus niger* glucoamylase linker and starch-binding domain (SBD), preferably one having at least one of the following substitutions or combinations of substitutions: D165M; Y141W; Y141R; K136F;

K192R; P224A; P224R; S123H+Y141W; G20S+ Y141W; A76G+Y141W; G128D+Y141W; G128D+ D143N; P219C+Y141W; N142D+D143N; Y141W+ K192R; Y141W+D143N; Y141W+N383R; Y141W+ P219C+A265C; Y141W+N142D+D143N; Y141W+ K192R V410A; G128D+Y141W+D143N; Y141W+ D143N+P219C; Y141W+D143N+K192R; G128D+ D143N+K192R; Y141W+D143N+K192R+P219C; G128D+Y141W+D143N+K192R; or G128D+ Y141W+D143N+K192R+P219C, especially G128D+ D143N (using SEQ ID NO: 13 for numbering).;

optionally iii) cellulolytic enzyme composition derived from a strain of *Trichoderma reesei*; preferably a cellulolytic composition derived from *Trichoderma reesei* further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y and optionally *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein;

optionally iv) a protease from *Thermoascus aurantiacus*, or a variant thereof and/or *Pyrococcus furiosus*;

wherein the fermenting organism is a *Saccharomyces* strain providing:

an ethanol yield boost compared to ETHANOL RED™;
lower glycerol production compared to ETHANOL RED™;

under the same fermentation conditions; preferably wherein the fermenting organism provides an ethanol yield boost of at least 0.5%, preferably at least 1.0%, more preferably at least 1.2%, even more preferably at least 1.5%, such as between 0.5-5%, e.g., 1.0-3.0%, after 72 hours at the conditions defined in Example 2, compared to ETHANOL RED™; and/or wherein the fermenting organism provides a lower glycerol production of at least 5%, preferably at least 10%, more preferably at least 15%, such as between 5-25%, such as 10-20% after 72 hours, at the conditions defined in Example 3, compared to ETHANOL RED™; in particular wherein the fermenting organism is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia); and/or wherein the fermenting organism is selected from the group of derivatives of *Saccharomyces cerevisiae* MBG 4911, MBG4913 or MBG4914 having the defining characteristics of one or more of these *Saccharomyces cerevisiae* strains.

[55]. The process of any of paragraphs [1]-[54], wherein the ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase:mg EP alpha-amylase).

[56]. The process of paragraphs [1]-[55], wherein the saccharification and fermentation are carried out simultaneously.

[57]. The process of any of paragraphs [1]-[56], wherein an enzyme composition of paragraphs 1-61 is used as the enzymes in saccharification or fermentation or simultaneous saccharification and fermentation.

[58]. A *Saccharomyces* yeast strain providing:
higher ethanol yield compared to ETHANOL RED™
lower glycerol production compared to ETHANOL RED™;
under the same fermentation conditions.

[59]. The strain of paragraph [58], wherein the yeast strain grows on xylose as a sole carbon source, e.g., determined using the Test T1.

[60]. The strain of paragraph [59], wherein the yeast strain shows more than two-fold increase in biomass, such as more than six-fold increase in biomass, such as more than 20-fold increase in biomass determined using the Test T1.

[61]. The strain of any of paragraphs [58]-[60], wherein the yeast strain has the following defining characteristics:
provides an ethanol yield boost of at least 0.5%, preferably at least 1.0%, more preferably at least 1.5%, more preferably at least 2.0%, more preferably at least 3.0%, more preferably at least 4.0%, even more preferably at least 5.0%, such as between 0.5-10%, e.g., between 1-6%, after 88 hours, at the conditions defined in Example 3 or Example 4, compared to ETHANOL RED™.

[62]. The strain of any of paragraphs [58]-[61], wherein the yeast strain has the following defining characteristics:
provides a lower glycerol production of at least 5%, preferably at least 10%, more preferably 15%, even more preferably at least 15%, more preferably at least 20%, such as between 4 and 40%, such as between 10 and 30% after 88 hours, at the conditions defined in Example 3 or Example 4, compared to ETHANOL RED™.

[63]. The strain of any of paragraphs [58]-[62], wherein the yeast strain is selected from the group consisting of *Saccharomyces cerevisiae* MBG4911 (deposited as V15/001459 at National Measurement Institute, Victoria, Australia), *Saccharomyces cerevisiae* MBG4913 (deposited as V15/001460 at National Measurement Institute, Victoria, Australia), and *Saccharomyces cerevisiae* MBG4914 (deposited as V15/001461 at National Measurement Institute, Victoria, Australia).

[64]. The strain of any of paragraphs [58]-[63], wherein the yeast strain is selected from the group of derivatives of *Saccharomyces cerevisiae* MBG4911, MBG4913 or MBG4914 having the defining characteristics of one or more of these *Saccharomyces cerevisiae* strains.

[65]. The strain of any of paragraphs [58]-[64], wherein the *Saccharomyces cerevisiae* strain is in a viable form, such as in particular dry yeast, cream yeast or compressed yeast.

[66]. A method of producing a derivative of strain *Saccharomyces cerevisiae* MBG4911, MBG4913 or MBG4914, respectively, which exhibits the defining characteristics of strains *Saccharomyces cerevisiae* MBG 4911, MBG4913 or MBG4914, respectively, comprising:
(a) providing:
(i) a first yeast strain; and
(ii) a second yeast strain, wherein the second yeast strain is a strain of the invention, in particular strain *Saccharomyces cerevisiae* MBG4911, MBG4913 or MBG4914, respectively, or a derivative of strain *Saccharomyces cerevisiae* MBG 4911, MBG4913 or MBG4914, respectively;

(b) culturing the first yeast strain and the second yeast strain under conditions which permit combining of DNA between the first and second yeast strains;

(c) screening or selecting for a derivative strain.

[67]. The method of paragraph [66], wherein step (c) comprises screening or selecting for a hybrid strain which exhibits one or more defining characteristic of strain *Saccharomyces cerevisiae* MBG4911, MBG4913 or MBG4914, respectively.

[68]. The method of paragraphs [66] or [67], comprising the further step of:

(d) repeating steps (b) and (c) with the screened or selected strain from step (c) as the first and/or second strain, until a derivative is obtained which exhibits the defining characteristics of strain *Saccharomyces cerevisiae* MBG4911, MBG4913 or MBG4914, respectively.

[69]. The method of paragraph [66]-[68], wherein the culturing step (b) comprises:

(i) sporulating the first yeast strain and the second yeast strain;

(ii) hybridizing germinated spores produced by the first yeast strain with germinated spores produced by the second yeast strain.

[70]. A *Saccharomyces* strain produced by the method of any of paragraphs [66]-[69].

[71]. A method of producing ethanol, comprising incubating a strain of any of paragraphs [58]-[70] with a substrate comprising a fermentable sugar under conditions which permit fermentation of the fermentable sugar to produce ethanol.

[72]. Use of a strain of paragraph [58]-[70] in the production of ethanol.

[73]. Use of strain *Saccharomyces cerevisiae* MBG4911, MBG4913 or MBG4914, respectively, in the production of a *Saccharomyces* strain which exhibits one or more defining characteristics of strain *Saccharomyces cerevisiae* MBG 4911, MBG4913 or MBG4914, respectively.

[74]. Use of strain *Saccharomyces cerevisiae* MBG4911, MBG4913 or MBG4914, respectively, or a derivative strain thereof in a process according to any of paragraphs [1]-[57].

[75]. A composition comprising a *Saccharomyces* yeast strain of any of paragraphs [58]-[65] and one or more components selected from the group consisting of: surfactants, emulsifiers, gums, swelling agents, and antioxidants.

[76]. The composition of paragraph [75], wherein the *Saccharomyces* yeast strain is 30 *Saccharomyces* MBG4911, MBG4913 or MBG4914.

[77]. The composition of paragraphs [75] or [76], wherein the *Saccharomyces* yeast strain is in a viable form, such as in particular in dry, cream or compressed form.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Materials & Methods
Materials:
PsAMG: Glucoamylase derived from *Pycnoporus sanguineus* disclosed as shown in SEQ ID NO: 4 in WO 2011/066576 and in SEQ ID NO: 17 herein.
TcAMG: Glucoamylase derived from *Trametes cingulata* shown in SEQ ID NO: 12 herein or SEQ ID NO: 2 in WO 2006/69289.
JA126: Alpha-amylase derived from *Rhizomucor pusillus* with an *Aspergillus niger* glucoamylase linker and starch-binding domain (SBD) shown in SEQ ID NO: 13 herein.
AAPE096: Alpha-amylase derived from *Rhizomucor pusillus* with an *Aspergillus niger* glucoamylase linker and starch-binding domain (SBD) shown in SEQ ID NO: 13 herein, with the following substitutions: G128D+D143N.
Yeast:
ETHANOL RED™ ("ER"): *Saccharomyces cerevisiae* yeast available from Fermentis (A Lesaffre Division), USA.
*Saccharomyces* MBG4911, MBG4913 and MBG4914: Non-recombinant *Saccharomyces* 30 *cerevisiae* yeast strains deposited by Microbiogen Pty Ltd, Unit E2, Lane Cove Business Park, 16 Mars Road, Lane Cove, NSW 2066, Australia under the terms of the Budapest Treaty with the National Measurement Institute, Victoria, Australia) and given the following accession number:

| Deposit | Accession Number | Date of Deposit |
|---|---|---|
| MBG4911 | V15/001459 | Jan. 13, 2015; |
| MBG4913 | V15/001460 | Jan. 13, 2015; |
| MBG4914 | V15/001461 | Jan. 13, 2015; |
| ETHANOL RED ™ | V14/007039 | Mar. 19, 2014. |

The strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposits represent substantially pure cultures of the deposited strains. The deposits are available as required by foreign patent laws in countries wherein counterparts of the subject application, or its progeny are filed. However, it should be understood that the availability of deposits do not constitute a license to practice the subject invention in derogation of patent rights granted by governmental action.

Methods:
Identity

The relatedness between two amino acid sequences or between two polynucleotide sequences is described by the parameter "identity".

For purposes of the present invention, the degree of identity between two amino acid sequences is determined by the Clustal method (Higgins, 1989, CAB/OS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two polynucleotide sequences is determined by the Wilbur-Lipman method (Wilbur and Lipman, 1983, Proceedings of the National Academy of Science USA 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

SIGMA Enzymatic Assay for Trehalase

One SIGMA unit will convert 1.0 micro mol of trehalose to 2.0 micro mol of glucose per minutes at pH 5.7 at 37° C. (liberated glucose determined at pH 7.5).

Glucoamylase Activity

Glucoamylase activity may be measured in Glucoamylase Units (AGU).

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-Amylase Activity

When used according to the present invention the activity of an acid alpha-amylase may be measured in AFAU (Acid Fungal Alpha-amylase Units) or FAU-F.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

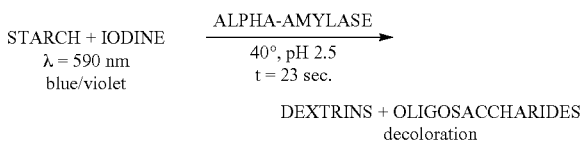

Standard Conditions/Reaction Conditions:

| Substrate: | Soluble starch, approx. 0.17 g/L |
|---|---|
| Buffer: | Citrate, approx. 0.03M |
| Iodine (I2): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Measurement of Cellulase Activity Using Filter Paper Assay (FPU Assay)

1. Source of Method
1.1 The method is disclosed in a document entitled "Measurement of Cellulase Activities" by Adney, B. and Baker, J. 1996. Laboratory Analytical Procedure, LAP-006, National Renewable Energy Laboratory (NREL). It is based on the IUPAC method for measuring cellulase activity (Ghose, T. K., Measurement of Cellulse Activities, Pure & Appl. Chem. 59, pp. 257-268, 1987.

2. Procedure 2.1 The method is carried out as described by Adney and Baker, 1996, supra, except for the use of a 96 well plates to read the absorbance values after color development, as described below.

2.2 Enzyme Assay Tubes:

2.2.1 A rolled filter paper strip (#1 Whatman; 1×6 cm; 50 mg) is added to the bottom of a test tube (13×100 mm).

2.2.2 To the tube is added 1.0 mL of 0.05 M Na-citrate buffer (pH 4.80).

2.2.3 The tubes containing filter paper and buffer are incubated 5 min. at 50° C. (±0.1° C.) in a circulating water bath.

2.2.4 Following incubation, 0.5 mL of enzyme dilution in citrate buffer is added to the tube. Enzyme dilutions are designed to produce values slightly above and below the target value of 2.0 mg glucose.

2.2.5 The tube contents are mixed by gently vortexing for 3 seconds.

2.2.6 After vortexing, the tubes are incubated for 60 mins. at 50° C. (±0.1° C.) in a circulating water bath.

2.2.7 Immediately following the 60 min. incubation, the tubes are removed from the water bath, and 3.0 mL of DNS reagent is added to each tube to stop the reaction. The tubes are vortexed 3 seconds to mix.

2.3 Blank and Controls 2.3.1 A reagent blank is prepared by adding 1.5 mL of citrate buffer to a test tube.

2.3.2 A substrate control is prepared by placing a rolled filter paper strip into the bottom of a test tube, and adding 1.5 mL of citrate buffer.

2.3.3 Enzyme controls are prepared for each enzyme dilution by mixing 1.0 mL of citrate buffer with 0.5 mL of the appropriate enzyme dilution.

2.3.4 The reagent blank, substrate control, and enzyme controls are assayed in the same manner as the enzyme assay tubes, and done along with them.

2.4 Glucose Standards 2.4.1 A 100 mL stock solution of glucose (10.0 mg/mL) is prepared, and 5 mL aliquots are frozen. Prior to use, aliquots are thawed and vortexed to mix.

2.4.2 Dilutions of the stock solution are made in citrate buffer as follows:

G1=1.0 mL stock+0.5 mL buffer=6.7 mg/mL=3.3 mg/0.5 mL

G2=0.75 mL stock+0.75 mL buffer=5.0 mg/mL=2.5 mg/0.5 mL

G3=0.5 mL stock+1.0 mL buffer=3.3 mg/mL=1.7 mg/0.5 mL

G4=0.2 mL stock+0.8 mL buffer=2.0 mg/mL=1.0 mg/0.5 mL 2.4.3 Glucose standard tubes are prepared by adding 0.5 mL of each dilution to 1.0 mL of citrate buffer.

2.4.4 The glucose standard tubes are assayed in the same manner as the enzyme assay tubes, and done along with them.

2.5 Color Development 2.5.1 Following the 60 min. incubation and addition of DNS, the tubes are all boiled together for 5 mins. in a water bath.

2.5.2 After boiling, they are immediately cooled in an ice/water bath.

2.5.3 When cool, the tubes are briefly vortexed, and the pulp is allowed to settle. Then each tube is diluted by adding 50 microL from the tube to 200 microL of ddH2O in a 96-well plate. Each well is mixed, and the absorbance is read at 540 nm.

2.6 Calculations (Examples are Given in the NREL Document)

2.6.1 A glucose standard curve is prepared by graphing glucose concentration (mg/0.5 mL) for the four standards (G1-G4) vs. $A_{540}$. This is fitted using a linear regression (Prism Software), and the equation for the line is used to determine the glucose produced for each of the enzyme assay tubes.

2.6.2 A plot of glucose produced (mg/0.5 mL) vs. total enzyme dilution is prepared, with the Y-axis (enzyme dilution) being on a log scale.

2.6.3 A line is drawn between the enzyme dilution that produced just above 2.0 mg glucose and the dilution that produced just below that. From this line, it is determined the enzyme dilution that would have produced exactly 2.0 mg of glucose.

2.6.4 The Filter Paper Units/mL (FPU/mL) are calculated as follows:

FPU/mL=0.37/enzyme dilution producing 2.0 mg glucose

Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e. 25° C., pH 5.5 and 10 min. reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease Assay Method (LAPU)

1 Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298.02/01 available from Novozymes A/S Denmark on request.

Test T1

Step 1: Yeast strains are streaked onto 2% w/v D-glucose 1% bacteriological peptone and 0.5% yeast extract medium solidified with 2% agar using standard microbiological techniques.

Step 2: After incubation for 72 hours at 30° C., yeast cells are taken from plates using a sterile microbiological loop and inoculated to an $OD_{600}$ (Optical Density at 600 nm) of between 0.1 and 0.2 units ($OD_{600}$ at $T_0$) in 50 ml of broth containing xylose (5% w/v), Difco Yeast Nitrogen Base w/o amino acids (0.67%), citric acid (0.3%) and trisodium citrate (0.7%) in distilled water in a 250 ml Erlenmeyer flask. An $OD_{600}$ of 0.1 unit is equal to approximately $9\times10^5$ yeast cells/mL. D-(+)-Xylose, minimum 99% can be obtained from Sigma-Aldrich.

Step 3: Cultures are incubated at 30° C. with shaking at 220 rpm (10 cm orbital diameter) for 48 hours.

Step 4: After 48 hours incubation, $OD_{600}$ of culture is measured ($OD_{600}$ at $T_{48}$).

Step 5: The fold increase in biomass is determined by the equation:

$$OD_{600} \text{ at } T_{48}/OD_{600} \text{ at } T_0.$$

EXAMPLES

Example 1

Production of *Saccharomyces* MBG4911, MBG4913 and MBG4914

Novel *Saccharomyces cerevisiae* MBG4911, MBG4913 and MBG4914 were produced using the methods described in WO 2005/121337 and through matings with various strains of *Saccharomyces cerevisiae* combined with selection for characteristics including low glycerol production and high ethanol production in a raw starch ethanol production process. Strains MBG4911, MBG4913 and MBG4914 were verified to be 35 *Saccharomyces cerevisiae* strains by their abilities to sporulate and produce progeny when the germinated spores were mated with standard strains of *Saccharomyces cerevisiae*, including haploid tester strains of *Saccharomyces cerevisiae*. One such haploid tester strain is W303-1A. Specifically, germinated spores of strains MBG4911, MBG4913 and MBG4914 were able to produce hybrid progeny when mated with tester strain W303-1A.

In more detail, haploid strain W303-1A was obtained from the Yeast Genetic Stock Center at the ATCC, USA (ATCC #208352). Strains MBG4911, MBG4913 and MBG4914 were cultured to form haploid *Saccharomyces* yeast as described in Ausubel, F. M. et al. (1997), Current Protocols in Molecular Biology, Volume 2, pages 13.2.1 to 13.2.5, published by John Wiley & Sons. Subsequently, the spores were germinated on a solid medium such as GYP containing 1% w/v D-glucose, 0.5% yeast extract, 1% w/v bacteriological peptone and 1.5% w/v agar and incubated at 30° C. for three to five days. The isolated germinated spores from strains MBG4911, MBG4913 and MBG4914 were then mated together with haploid W303-1A using the method described in, for example, Ausubel, F. M. et al. (1997), Current Protocols in molecular Biology, Volume 2, pages 13.2.1 to 13.2.5, published by John Wiley & Sons. Formation of hybrid zygotes could be observed under a microscope demonstrating that Strains MBG 4911, 4913 and 4914 are *Saccharomyces cerevisiae* strains.

Strains MBG4911, MBG4913 and MBG4914 were deposited on 19 Jan. 2015 at the National Measurement Institute, 1/153 Bertie Street, Port Melbourne, Victoria 3207, Australia under the Budapest Treaty. Strain MBG4911 was designated accession number V15/001459, strain MBG4913 was designated accession number V15/001460, and strain MBG4914 was designated accession number V15/001461. The commercially available *Saccharomyces cerevisiae* known as ETHANOL RED™ was used for comparison in Example 2. ETHANOL RED™ yeast strain was deposited on Mar. 19, 2014 at the National Measurement Institute, 1/153 Bertie Street, Port Melbourne, Victoria 3207, Australia, under the Budapest Treaty and was designated accession number V14/007039.

Example 2

Growth of *Saccharomyces* MBG4911, MBG4913 and MBG4914 in Xylose Minimal Media

Growth of strains MBG4911, MBG4913 and MBG4914 on xylose as a sole carbon source was determined using Test T1. *Saccharomyces cerevisiae* strains MBG4911, MBG4913 and MBG4914 were streaked onto 2% w/v D-glucose 1% bacteriological peptone and 0.5% yeast extract medium (GYP) solidified with 2% agar using standard microbiological techniques. After incubation for 72 hours at 30° C., yeast cells were taken from plates using a sterile microbiological loop and inoculated to an $OD_{600}$ (Optical Density at 600 nm) of between 0.1 and 0.2 units ($OD_{600}$ at T0) in 50 ml of broth. An $OD_{600}$ of 0.1 unit is equal to approximately $9 \times 10^5$ yeast cells/mL. The broth contained xylose (5% w/v), Difco Yeast Nitrogen Base w/o amino acids (0.67%), citric acid (0.3%) and tri-sodium citrate (0.7%) in distilled water in a 250 ml Erlenmeyer flask. Citric acid and tri-sodium citrate were provided as buffering agents that are not able to be used as growth substrates by *Saccharomyces*. D-(+)-Xylose 99% pure was obtained from Sigma-Aldrich (catalogue number X1500-500G). Cultures were incubated at 30° C. with shaking at 220 rpm (10 cm orbital diameter) for 48 hours prior to measuring $OD_{600}$ ($OD_{600}$ at $T_{48}$ hrs). The fold increase in biomass was determined by the equation: $OD_{600}$ at $T_{48}$ hrs divided by $OD_{600}$ at $T_0$.

Strain MBG4911 showed greater than two-fold increase in biomass, whilst MBG4913 showed more than 20-fold increase in biomass, and MBG 4914 showed greater than six-fold increase in biomass in 48 hours. Under the same conditions the ETHANOL RED™ yeast (Budapest Treaty accession number V14/007039) failed to increase in biomass.

Example 3

Improved Ethanol Yield and Reduced Glycerol Production in 500 g Kettle Scale RSH Fermentations All fermentations were done in 500 ml stirred glass kettle reactors placed in a waterbath.

Mash Preparation

Yellow dent corn (obtained from GPRE in Central City, Nebr. in November 2014; ground in-house) was mixed with tap water and the dry solids (DS) level was determined to be 33.5% by moisture balance. This mixture was supplemented with 3 ppm Lactrol and 500 ppm urea. The slurry was adjusted to pH 4.5 with 40% $H_2SO_4$.

Yeast Strains and Preparation

The four yeast strains tested in this experiment were ETHANOL RED™ (Fermentis), *Saccharomyces* MBG4911, MBG4913, and MBG4914. Yeasts were rehydrated by weighing approximately 5 g of dried yeast into 50 ml of 36.5° C. tap water in a 125 mL Erlenmeyer flask. The flasks were then covered with parafilm and allowed to incubate in a 36.5° C. water bath. Flasks were swirled at the beginning and end of rehydration to mix, but no other agitation took place. After a total of 20 minutes, the flasks were removed from the water bath. Each yeast was enumerated using the YC-100 (Yeast Cell Counter, Chemometer).

Simultaneous Saccharification and Fermentation (SSF)

TcAMG/JA126 (ratio between AGU and FAU-F about 10:1) was dosed to each reactor at 0.51 AGU/gDS. Yeast was added at a pitch of 5 million cells per gram. Water was added to each kettle such that the total volume added to each kettle was equal. Fermentations took place at 32° C. for 88 hours.

HPLC Analysis

Fermentation sampling took place by sampling 5 grams of mash into 15 ml tubes at 16, 24, 40, 48, 64, 72, and 88 hours of fermentation. Each tube was processed for HPLC analysis by deactivation with 150 µL of 40% v/v $H_2SO_4$, vortexing, centrifuging at 1460×g for 10 minutes, and filtering through a 0.45 μm Whatman PP filter, followed by a 0.2 μm Whatman PP filter. Samples were stored at 4° C. prior to and during HPLC analysis.

TABLE 1

HPLC System

| | |
|---|---|
| HPLC System | Agilent's 1100/1200 series with Chem station software<br>Degasser, Quaternary Pump, Auto-Sampler, Column Compartment/w Heater<br>Refractive Index Detector (RI) |
| Column | Bio-Rad HPX- 87H Ion Exclusion Column<br>300 mm × 7.8 mm part# 125-0140<br>Bio-Rad guard cartridge Cation H part# 125-0129,<br>Holder part# 125-0131 |
| Method | 0.005M $H_2SO_4$ mobile phase<br>Flow rate: 0.6 ml/min<br>Column temperature: 65° C.<br>RI detector temperature: 55° C. |

Samples were analyzed for sugars (DP4+, DP3, DP2, glucose, and fructose), organic acids (lactic and acetic), glycerol, and ethanol.

Increased Ethanol and Faster Kinetics Results

Ethanol titers at 64, 72, and 88 hours of fermentation are shown in Table 2 below. These strains show increased kinetics, including increased speed of fermentation as evidenced by boosts exhibited at 64 and 72 hours, even when compared to the ethanol titers produced by Ethanol Red™ (ER) (Fermentis) at 88 hours of fermentation time.

TABLE 2

Ethanol Titers and Comparative Boosts during the later stages of fermentation

| Time (hours) | ER | MBG4911 | MBG4913 | MBG4914 |
|---|---|---|---|---|
| | Ethanol (w/v %) | | | |
| 64 | 14.946 | 15.362 | 15.400 | 15.403 |
| 72 | 15.058 | 15.354 | 15.423 | 15.372 |
| 88 | 15.182 | 15.330 | 15.499 | 15.505 |
| % Boost Compared to Ethanol Red at Same Time Point | | | | |
| 64 | 0 | 2.78 | 3.03 | 3.05 |
| 72 | 0 | 1.97 | 2.42 | 2.08 |
| 88 | 0 | 0.97 | 2.08 | 2.13 |
| % Boost Compared to ER at Final Time Point | | | | |
| 64 | −1.55 | 1.18 | 1.43 | 1.45 |
| 72 | −0.82 | 1.13 | 1.58 | 1.25 |
| 88 | 0.00 | 0.97 | 2.08 | 2.13 |

Reduced Glycerol Results

Glycerol levels at the later stages of fermentation are shown in Table 3 below.

TABLE 3

Glycerol Titers and Comparisons during the later stages of fermentation.

| Time (hours) | ER | MBG4911 | MBG4913 | MBG4914 |
|---|---|---|---|---|
| | Glycerol (w/v %) | | | |
| 64 | 0.922 | 0.755 | 0.872 | 0.809 |
| 72 | 0.927 | 0.753 | 0.877 | 0.814 |
| 88 | 0.935 | 0.755 | 0.889 | 0.819 |
| | Comparison of Glycerol Levels to ER (%) | | | |
| 64 | 0 | −18.07 | −5.34 | −12.19 |
| 72 | 0 | −18.75 | −5.35 | −12.18 |
| 88 | 0 | −19.25 | −5.00 | −12.46 |

Example 4

Improved Ethanol Yield and Reduced Glycerol Production in 500 g Kettle Scale RSH Fermentations with Varying RSH Enzyme All fermentations were done in 500 ml stirred glass kettle reactors placed in a waterbath.

Mash Preparation

Yellow dent corn (obtained from GPRE in Central City, Nebr. in November 2014; ground in-house) was mixed with tap water and the dry solids (DS) level was determined to be 34.4% by moisture balance. This mixture was supplemented with 3 ppm Lactrol and 500 ppm urea. The slurry was adjusted to pH 4.5 with 40% $H_2SO_4$.

Yeast Strains and Preparation

The four yeast strains tested in this experiment were ETHANOL RED™ (Fermentis), Saccharomyces MBG4911, MBG4913, and MBG4914. Yeasts were rehydrated by weighing approximately 5 g of dried yeast into 50 ml of 36.5° C. tap water in a 125 mL Erlenmeyer flask. The flasks were then covered with parafilm and allowed to incubate in a 36.5° C. water bath. Flasks were swirled at the beginning and end of rehydration to mix, but no other agitation took place. After a total of 20 minutes, the flasks were removed from the water bath. Each yeast was enumerated using the YC-100.

Simultaneous Saccharification and Fermentation (SSF)

PsAMG/AAPE096 (ratio between AGU and FAU-F about 16:1) was dosed to each tube of mash at 0.39 AGU/gDS or Tc/JA126 (ratio about 10:1) was dosed at 0.23 AGU/gDS. Yeast was dosed at 5×10e6 cells/g mash. Milli-Q water was added to each tube so that a total volume of liquid added (enzyme+MQ water) to each tube would be equally proportionate to the mash weight. Fermentations took place in a 32° C. water bath for 88 hours.

HPLC Analysis

Fermentation sampling took place by sampling 5 grams of mash into 15 ml tubes at 24, 40, 47, 64, 70, and 88 hours of fermentation. Each tube was processed for HPLC analysis by deactivation with 150 μL of 40% v/v $H_2SO_4$, vortexing, centrifuging at 1460×g for 10 minutes, and filtering through a 0.45 μm Whatman PP filter, followed by a 0.2 μm Whatman PP filter. Samples were stored at 4° C. prior to and during HPLC analysis.

TABLE 4

HPLC System

| | |
|---|---|
| HPLC System | Agilent's 1100/1200 series with Chem station software<br>Degasser, Quaternary Pump, Auto-Sampler, Column Compartment/w Heater<br>Refractive Index Detector (RI) |

TABLE 4-continued

HPLC System

| | |
|---|---|
| Column | Bio-Rad HPX- 87H Ion Exclusion Column 300 mm × 7.8 mm part# 125-0140 |
| | Bio-Rad guard cartridge Cation H part# 125-0129, |
| | Holder part# 125-0131 |
| Method | 0.005M $H_2SO_4$ mobile phase |
| | Flow rate: 0.6 ml/min |
| | Column temperature: 65° C. |
| | RI detector temperature: 55° C. |

Samples were analyzed for sugars (DP4+, DP3, DP2, glucose, and fructose), organic acids (lactic and acetic), glycerol, and ethanol.

Increased Ethanol Results

Ethanol titers and boosts compared to "ER" are shown in Table 5 below.

TABLE 5

Ethanol Titers and Boosts Compared to ER at 88 hours

| TcAMG/JA126 | ER | MBG4911 | MBG4913 | MBG4914 |
|---|---|---|---|---|
| | \multicolumn{4}{c}{Ethanol Titer (w/v %)} | | | |
| | 15.267 | 15.816 | 15.647 | 15.582 |
| | \multicolumn{4}{c}{% Boost compared to ER} | | | |
| | 0 | 3.60 | 2.49 | 2.07 |

TABLE 5-continued

Ethanol Titers and Boosts Compared to ER at 88 hours

| PsAMG/AAPE096 | ER | MBG4911 | MBG4913 | MBG4914 |
|---|---|---|---|---|
| | \multicolumn{4}{c}{Ethanol Titer (w/v %)} | | | |
| | 15.360 | 16.249 | 16.097 | 16.010 |
| | \multicolumn{4}{c}{% Boost compared to ER} | | | |
| | 0 | 5.79 | 4.80 | 4.23 |

Reduced Glycerol Results

Glycerol titers and comparisons to "ER" at 88 hours are shown in Table 6 below.

TABLE 3

88 hour Glycerol Titers and Comparisons to ER

| TcAMG/JA126 | ER | MBG4911 | MBG4913 | MBG4914 |
|---|---|---|---|---|
| | \multicolumn{4}{c}{Glycerol Titer (w/v %)} | | | |
| | 1.000 | 0.760 | 0.880 | 0.847 |
| | \multicolumn{4}{c}{Comparison to ER (%)} | | | |
| | 0 | −24.01 | −12.00 | −15.30 |
| PsAMG/AAPE096 | ER | MBG4911 | MBG4913 | MBG4914 |
| | \multicolumn{4}{c}{Glycerol Titer (w/v %)} | | | |
| | 0.992 | 0.781 | 0.919 | 0.865 |
| | \multicolumn{4}{c}{Comparison to ER (%)} | | | |
| | 0 | −21.25 | −7.34 | −12.78 |

---

The invention claimed is:

1. A process of producing ethanol from starch-containing material, the process comprising:
   (a) saccharifying starch-containing material at a temperature below the initial gelatinization temperature; and
   (b) fermenting using a fermentation organism;
      wherein saccharification and/or fermentation is done in the presence of a glucoamylase and an alpha-amylase;
      wherein the fermenting organism is:
      Saccharomyces cerevisiae MBG4911 (deposited as V15/001459 at National Measurement Institute, Victoria, Australia);
      Saccharomyces cerevisiae MBG4913 (deposited as V15/001460 at National Measurement Institute, Victoria, Australia); or
      Saccharomyces cerevisiae MBG4914 (deposited as V15/001461 at National Measurement Institute, Victoria, Australia).

2. The process of claim 1, wherein the fermenting organism is capable of growing on xylose as a sole carbon source.

3. The process of claim 1, wherein the fermenting organism provides an ethanol yield boost of at least 0.5% after 88 hours compared to the ETHANOL RED™ Saccharomyces cerevisiae strain deposited as V14/007039 at National Measurement Institute, Victoria, Australia under the same conditions.

4. The process of claim 1, wherein the fermenting organism provides a lower glycerol production of at least 5% after 88 hours compared to the ETHANOL RED™ Saccharomyces cerevisiae strain deposited as V14/007039 at National Measurement Institute, Victoria, Australia under the same conditions.

5. A Saccharomyces yeast strain selected from:
   Saccharomyces cerevisiae MBG4911 (deposited as V15/001459 at National Measurement Institute, Victoria, Australia);
   Saccharomyces cerevisiae MBG4913 (deposited as V15/001460 at National Measurement Institute, Victoria, Australia); and
   Saccharomyces cerevisiae MBG4914 (deposited as V15/001461 at National Measurement Institute, Victoria, Australia).

6. The yeast strain of claim 5, wherein the strain is capable of growing on xylose as a sole carbon source.

7. The yeast strain of claim 5, wherein the strain is capable of providing an ethanol yield boost of at least 0.5% after 88 hours compared to the ETHANOL RED™ Saccharomyces cerevisiae strain deposited as V14/007039 at National Measurement Institute, Victoria, Australia under the same conditions.

8. The yeast strain of claim 5, wherein the strain is capable of providing a lower glycerol production of at least 5% after 88 hours compared to the ETHANOL RED™ Saccharomyces cerevisiae strain deposited as V14/007039 at National Measurement Institute, Victoria, Australia under the same conditions.

9. A method of producing a derivative of strain Saccharomyces cerevisiae MBG4911, MBG4913 or MBG4914, the method comprising:
   (a) providing:
      (i) a first yeast strain; and
      (ii) a second yeast strain, wherein the second yeast strain is strain Saccharomyces cerevisiae MBG4911, MBG4913 or MBG4914;
   (b) culturing the first yeast strain and the second yeast strain under conditions which permit combining of DNA between the first and second yeast strains;
   (c) screening or selecting for a derivative strain.

10. The method of claim 9, wherein step (c) comprises screening or selecting for a hybrid strain which exhibits one or more defining characteristic of strain Saccharomyces cerevisiae MBG4911, MBG4913 or MBG4914.

11. The method of claim 9, comprising the further step of:
   (d) repeating steps (b) and (c) with the screened or selected strain from step (c) as the first and/or second strain, until a derivative is obtained which exhibits the defining characteristics of strain Saccharomyces cerevisiae MBG4911, MBG4913 or MBG4914.

12. The method of claim 9, wherein the culturing step (b) comprises:
   (i) sporulating the first yeast strain and the second yeast strain;
   (ii) hybridizing germinated spores produced by the first yeast strain with germinated spores produced by the second yeast strain.

13. A method of producing ethanol, comprising incubating the Saccharomyces yeast strain of claim 5 with a substrate comprising a fermentable sugar under conditions which permit fermentation of the fermentable sugar to produce ethanol.

14. A composition comprising a Saccharomyces yeast strain of claim 5 and one or more components selected from surfactants, emulsifiers, gums, swelling agents, and antioxidants.

15. A method of producing a recombinant derivative of the Saccharomyces yeast of claim 5, the method comprising introducing a nucleic acid into the Saccharomyces yeast of claim 5 using recombinant DNA technology.

16. The method of claim 15, wherein the nucleic acid is introduced into Saccharomyces cerevisiae MBG4911 (deposited as V15/001459 at National Measurement Institute, Victoria, Australia).

* * * * *